United States Patent
Itsuji

(10) Patent No.: US 7,852,466 B2
(45) Date of Patent: Dec. 14, 2010

(54) APPARATUS AND METHOD FOR OBTAINING INFORMATION RELATED TO TERAHERTZ WAVES

(75) Inventor: Takeaki Itsuji, Hiratsuka (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 12/426,979

(22) Filed: Apr. 21, 2009

(65) Prior Publication Data

US 2009/0231571 A1 Sep. 17, 2009

Related U.S. Application Data

(63) Continuation of application No. 12/193,121, filed on Aug. 18, 2008, now Pat. No. 7,551,269.

(30) Foreign Application Priority Data

Aug. 31, 2007 (JP) ............................. 2007-226338
Jun. 18, 2008 (JP) ............................. 2008-159315

(51) Int. Cl.
*G01J 11/00* (2006.01)
*G02F 1/01* (2006.01)

(52) U.S. Cl. ...................... 356/51; 356/450; 250/358.1; 250/338.1; 250/330; 324/71.5

(58) Field of Classification Search .................. 356/51, 356/450, 451, 456; 250/330, 338.1, 341.1, 250/358.1, 339.02, 339.06, 339.07, 341.3; 324/71.5, 96, 639

See application file for complete search history.

(56) References Cited

U.S. PATENT DOCUMENTS 5,789,750 A * 8/1998 Nuss ........................ 250/338.1
6,078,047 A * 6/2000 Mittleman et al. ....... 250/338.1

(Continued)

FOREIGN PATENT DOCUMENTS

EP    1 469 298 A1    10/2004

(Continued)

OTHER PUBLICATIONS

Extended European Search Report issued in the corresponding European Application No. 08 16 2232, dated Feb. 3, 2010.

(Continued)

*Primary Examiner*—Sang Nguyen
(74) *Attorney, Agent, or Firm*—Fitzpatrick, Cella, Harper & Scinto

(57) ABSTRACT

To provide an apparatus capable obtaining a temporal waveform of terahertz waves transmitted through or reflected by a sample in a set region. A delay unit is configured to change a timing at which the detection unit detects terahertz waves transmitted through or reflected by a sample, which is originated from terahertz waves generated by a generation unit. A waveform obtaining unit is configured to obtain a temporal waveform of the transmitted terahertz waves which are obtained by using the delay unit. The delay unit, of which more than one may be used, is controlled so that the detection unit detects the transmitted terahertz waves in an area related to the temporal waveform set on the basis of information related to the sample that is pre-stored in the storage unit. Then, a temporal waveform of the transmitted terahertz waves in the area is obtained.

11 Claims, 13 Drawing Sheets

U.S. PATENT DOCUMENTS

| | | | |
|---|---|---|---|
| 6,320,191 B1 * | 11/2001 | Rudd | 250/341.1 |
| 6,414,473 B1 * | 7/2002 | Zhang et al. | 324/96 |
| 6,665,075 B2 | 12/2003 | Mittleman et al. | 356/450 |
| 6,816,647 B1 * | 11/2004 | Rudd et al. | 385/37 |
| 6,828,558 B1 * | 12/2004 | Arnone et al. | 250/341.1 |
| 6,844,552 B2 | 1/2005 | Zhang et al. | 250/338.1 |
| 7,119,339 B2 | 10/2006 | Ferguson et al. | 250/358.1 |
| 2001/0029436 A1 * | 10/2001 | Fukasawa | 702/117 |
| 2005/0100866 A1 * | 5/2005 | Arnone et al. | 433/215 |
| 2006/0255277 A1 * | 11/2006 | Cole et al. | 250/341.1 |
| 2007/0215810 A1 | 9/2007 | Kurosaka et al. | 250/358.1 |
| 2007/0252992 A1 | 11/2007 | Itsuji | 356/369 |
| 2007/0273357 A1 | 11/2007 | Saito et al. | 324/71.5 |
| 2007/0279136 A1 | 12/2007 | Koyama et al. | 331/107 |
| 2007/0279143 A1 | 12/2007 | Itsuji | 331/185 |
| 2008/0013071 A1 | 1/2008 | Tsumura et al. | 356/51 |
| 2008/0048678 A1 | 2/2008 | Kurosaka et al. | 324/639 |
| 2008/0116374 A1 | 5/2008 | Ouchi et al. | 250/306 |
| 2008/0210873 A1 | 9/2008 | Itsuji | 250/347 |

FOREIGN PATENT DOCUMENTS

| | | |
|---|---|---|
| JP | 2004-003902 | 1/2004 |
| JP | 2004-28618 | 1/2004 |
| WO | WO 2006/054975 A1 | 5/2006 |

OTHER PUBLICATIONS

JA Zeitler et al., "Analysis of Coating Structures and Interfaces in Solid Oral Dosage Forms by Three Dimensional Terahertz Pulsed Imaging," *Journal of Pharmaceutical Sciences*, vol. 96, No. 2, Feb. 2007, pp. 330-340.

DA Zimdars, "Fiber-Pigtailed Terahertz Time Domain Spectroscopy Instrumentation for Package Inspection and Security Imaging," in *Terahertz for Military and Security Applications: Proceedings of the SPIE*, vol. 5070, RJ Hwu et al. eds., 2003, pp. 108-116.

YD Gong et al., "Terahertz Spectroscopy Technology Trend Using 1550-nm Ultrafast Fiber Laser," *Microwave and Optical Technology Letters*, vol. 49, No. 2, Feb. 2007, pp. 439-443.

* cited by examiner

MEASURED WAVEFORM

RECONSTRUCTED WAVEFORM

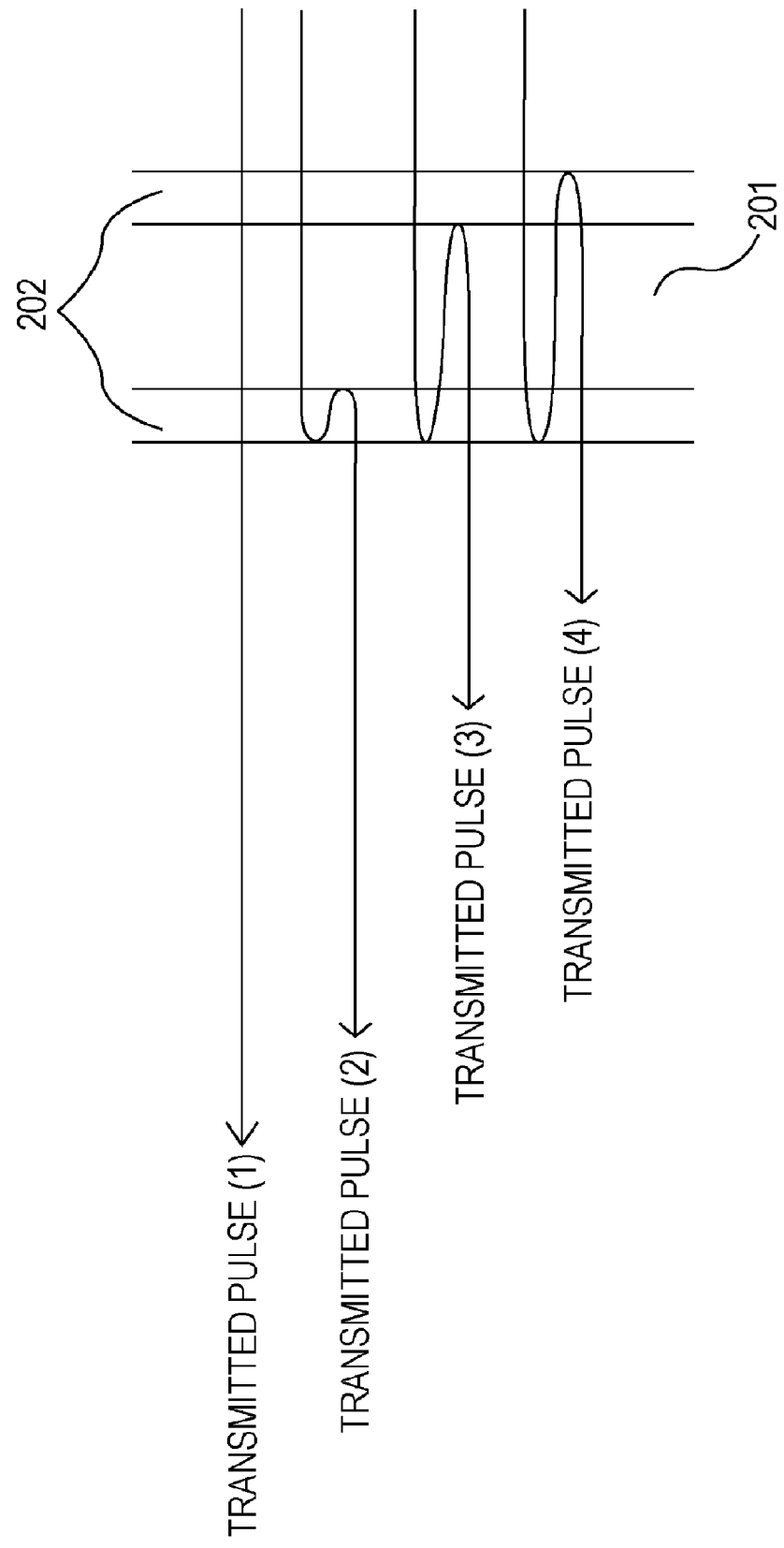

APPARATUS AND METHOD FOR OBTAINING INFORMATION RELATED TO TERAHERTZ WAVES

RELATED APPLICATIONS

This application is a continuation of patent application Ser. No. 12/193,121, filed Aug. 18, 2008, now U.S. Pat. No. 7,551,269, issued Jun. 23, 2009, claims benefit of the filing date of that patent under 35 U.S.C. §120, claims benefit of the filing dates of Japanese patent applications nos. 226338/2007 and 159315/2008, filed Aug. 31, 2007, and Jun. 18, 2008, respectively, under 35 U.S.C. §119, and incorporates the entire disclosure of each of the three mentioned prior patents/applications herein by reference.

BACKGROUND OF THE INVENTION

1. Field of the Invention

The present invention relates to an apparatus and a method of obtaining information related to terahertz waves that are transmitted through or reflected by a sample.

2. Description of the Related Art

A terahertz wave is an electromagnetic wave having an arbitrary frequency band from 0.03 THz to 30 THz. In a terahertz wave band, characteristic absorptions that depend on structures and states of various substances that include biological molecules occur. Utilizing such characteristics, an inspection technology for an analysis and an identification of a substance in a nondestructive manner has been developed. Also, an application to a safe imaging technology as a substitute for X-rays or a high-speed communication technology is expected.

In addition, the characteristics of terahertz waves include a moderate ability to penetrate a sample. For example, a technology for measuring a film thickness of a multilayer film, utilizing this property, is disclosed (Japanese Patent Laid-Open No. 2004-28618). According to Japanese Patent Laid-Open No. 2004-28618, on the basis of a plurality of terahertz wave pulse responses, the film thickness of the multilayer film is determined. These pulse responses are obtained by sampling a time response waveform of the terahertz wave with a probe light. According to this method, the sampling is carried out over all measurement time regions.

In recent years, one application of this property of terahertz waves has been a technology for measuring or inspecting the product quality of tablets in a nondestructive manner. For example, an application to a technology for measuring or inspecting the coating thicknesses of a sugar-coated tablet, a film-coated tablet, and the like is expected. These coating thicknesses affect the disintegration properties or resolvability of the tablets. Also, the tablets are formed by mixing a powdered medicinal agent and an additive. For that reason, an application to a technology for measuring or inspecting the uniformity of the contained amount of the medicinal agent with respect to the additive is hoped for.

These characteristic features directly affect medicinal effects of the tablets. For that reason, a technology for controlling and maintaining the product quality of the tablets is important. At the moment, for this purpose, a portion of the manufactured tablets is extracted, and a destructive inspection is carried out.

According to Japanese Patent Laid-Open No. 2004-28618, a method of shortening a period of time needed to measure the film thickness of the multilayer film is sought.

In addition, in a case where quality control for tablets is performed, instead of the sampling inspection, in future, it may be desired to effect a constant inspection during the manufacturing process, so that all the tablets can be inspected. In order to carry out such a process inspection, a method of measuring and inspecting the samples in a nondestructive manner is desirable, but a method by which this could be achieved has not yet been established. In particular, for the process inspection for medicinal tablets, from a standpoint that a large number of samples are dealt with in a short period of time, a method of monitoring the state of a single table in a still shorter period of time is ideal.

SUMMARY OF THE INVENTION

The present invention provides an apparatus capable obtaining a temporal waveform of terahertz waves which are transmitted through or reflected by a sample in a set region. Also, the present invention provides an apparatus capable shortening the period of time needed to obtain information related to the sample (film thickness or the like) by using the temporal waveform in the region as compared with a case of obtaining all regions of the temporal waveform.

In view of the above, the terahertz wave detection apparatus according to an aspect of the present invention has the following configuration: a detection unit arranged to detect a terahertz wave from a sample and an information storage unit arranged to previously store internal information which becomes a standard of the sample. The terahertz wave detection apparatus also includes a delay optical unit arranged to adjust a timing at which the detection unit is operated by changing a delay time with respect to a pump light of a probe light incident on the detection unit. The terahertz wave detection apparatus also includes a delay time adjustment unit arranged to set a measurement area desired to be measured on the basis of the information which becomes the standard in the storage unit and adjust the delay time in the measurement area. The terahertz wave detection apparatus also includes a reconstruction unit arranged to reconstruct the internal information on the sample on the basis of the output of the detection unit and an adjustment amount of the delay time by the delay time adjustment unit.

The terahertz wave detection method according to an aspect of the present invention has the following steps (a) to (e):

(a) previously storing internal information which becomes a standard of a sample;

(b) adjusting a timing of detecting a terahertz wave in a detection step by way of a delay time with respect to a pump light of a probe light;

(c) setting a measurement area desired to be measured on the basis of the information which becomes the standard in the information storage step and adjusting a delay time in a delay optical step in the measurement area;

(d) detecting the terahertz wave from the sample; and (e) reconstructing the internal information on the sample on the basis of an output in the detection step and an adjustment amount in the delay time adjustment step.

An inspection system according to an aspect of the present invention has the following configuration: a detection unit arranged to detect a terahertz wave from a sample and an information storage unit arranged to previously store internal information which becomes a standard of the sample. The inspection system also includes a delay optical unit arranged to adjust a delay time of a probe light incident on the detection unit with respect to a pump light. The inspection system also includes a delay time adjustment unit arranged to set a measurement area desired to be measured on the basis of the information which becomes the standard in the storage unit and adjust the delay time of the probe light in the measurement area. The inspection system also includes a processing unit arranged to reconstruct the internal information on the sample on the basis of an output of the detection unit and an adjustment amount of the delay time by the delay time adjustment unit. The inspection system also includes a comparison unit arranged to compare the internal information on the sample obtained by the processing unit with the internal information which becomes the standard of the sample stored in the information storage unit. The inspection system also includes an apparatus control unit arranged to carry out screening of the sample or adjust a manufacturing condition of the sample in accordance with the comparison result of the comparison unit.

An apparatus for obtaining information related to a terahertz wave transmitted through or reflected by a sample according to another aspect of the present invention includes: a generation unit arranged to generate a terahertz wave; a detection unit arranged to detect a terahertz wave transmitted through or reflected by a sample which is originated from the terahertz wave generated by the generation unit; a delay unit arranged to change a timing for the detection unit to detect the terahertz wave; a storage unit arranged to previously store information related to the sample; and a waveform obtaining unit arranged to obtain a temporal waveform of the transmitted or reflected terahertz wave which is obtained by the delay unit, in which the delay unit is controlled to allow the detection unit to detect the terahertz wave in an area related to the temporal waveform set on the basis of the information related to the sample previously stored in the storage unit, and a temporal waveform of the transmitted or reflected terahertz wave in the area is obtained.

A method of obtaining information related to a terahertz wave transmitted through or reflected by a sample according to another aspect of the present invention includes: generating a terahertz wave; detecting a terahertz wave transmitted through or reflected by a sample the terahertz wave which is originated from the generated terahertz wave; obtaining a temporal waveform of the transmitted or reflected terahertz wave by changing the detection timing; changing the timing so as to detect the transmitted or reflected terahertz wave in an area related to the previously obtained temporal waveform set on the basis of the temporal waveform of the terahertz wave transmitted through or reflected by the sample; and obtaining a temporal waveform of the transmitted or reflected terahertz wave in the area.

According to the various aspects of the present invention, the measurement reference related to the internal information which serves as the standard of the sample is pre-stored in the information storage unit, and on the basis of the measurement reference, the reaching time of the terahertz wave reaching the detection unit is predicted. According to the embodiments of the present invention, the delay time adjustment unit adjusts the delay time through switching in a discontinuous manner so that the delay time of the probe light for operating the detection unit corresponds to the reaching time of the terahertz wave. For that reason, it is possible efficiently to detect the terahertz wave necessary for obtaining the sought internal information on the sample (for example, the peak of the pulse of the reflected terahertz waves). On the basis of the output of the detection unit and the adjustment amount of the delay time adjustment unit, the processing unit computes the internal information on the sample. As in the mode of detecting only the necessary part on the basis of the measurement reference, it is possible to efficiently obtain internal information on the sample.

Further features of the present invention will become apparent from the following description of exemplary embodiments with reference to the attached drawings.

BRIEF DESCRIPTION OF THE DRAWINGS

FIG. 16 illustrates a propagation path example of a transmitted pulse wave according to the second embodiment of the present invention.

DESCRIPTION OF THE EMBODIMENTS

An apparatus and a method according to the preferred embodiments of the present invention will be described with reference to the drawings. It is noted that the present invention is not limited to these embodiments, and without departing from the scope of the present invention, modifications are not to be considered excluded from the present invention.

(Apparatus for Obtaining Information Related to Terahertz Wave)

Figure 1:
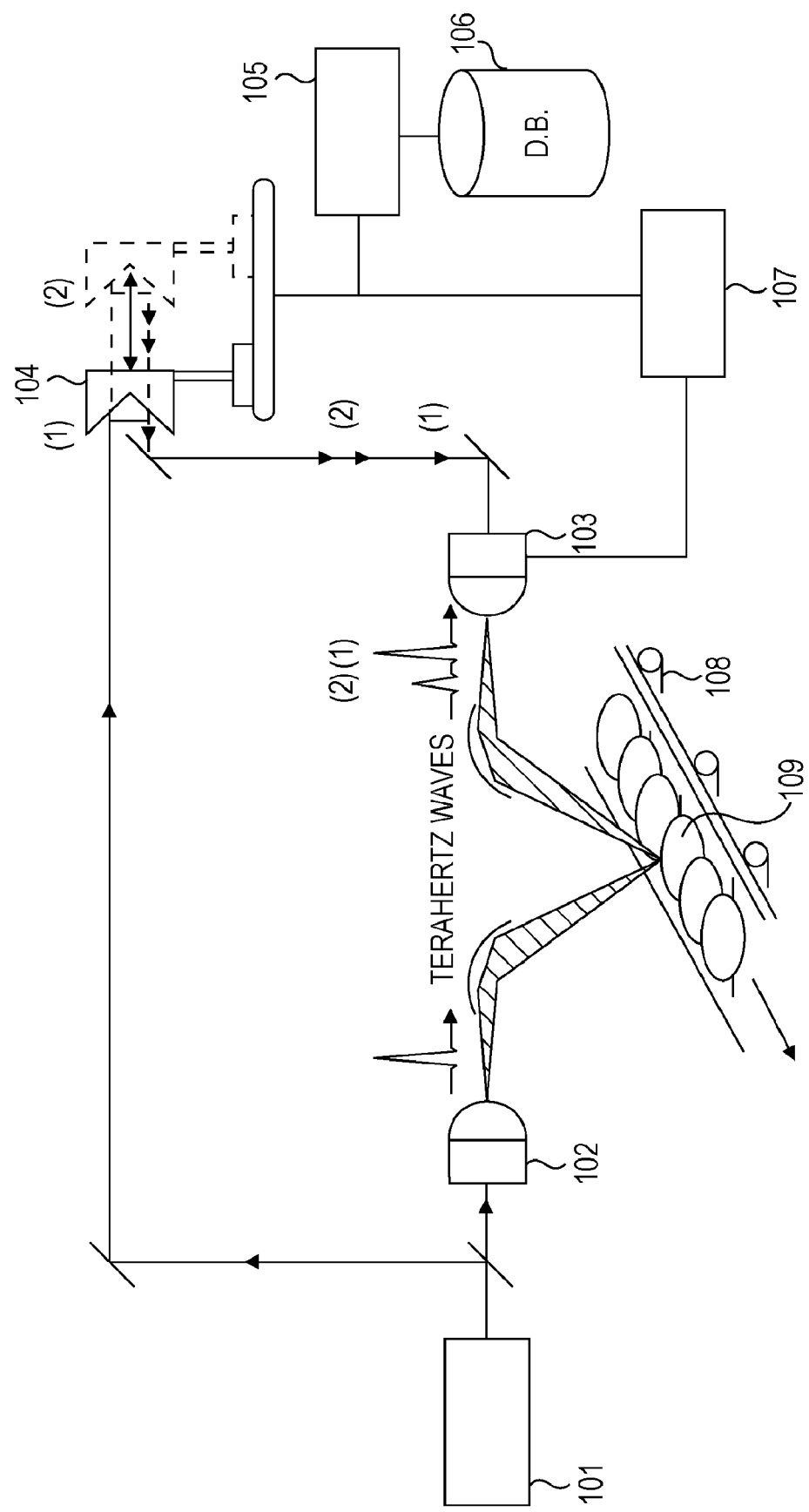
FIG. 1 is a schematic configuration diagram of an apparatus according to a first embodiment of the present invention.
Figure 17A:
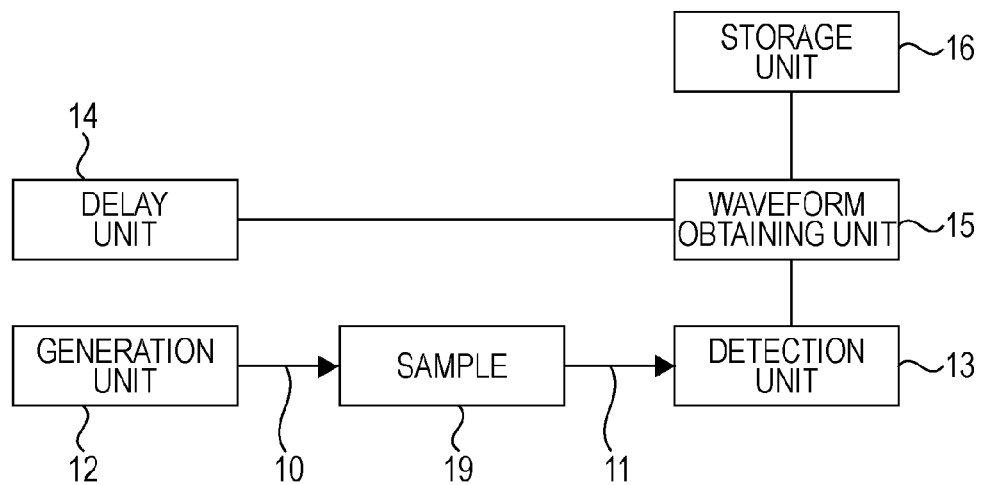
FIGS. 17A and 17B are schematic diagrams for describing an apparatus according to an embodiment of the present invention.
Figure 17B:
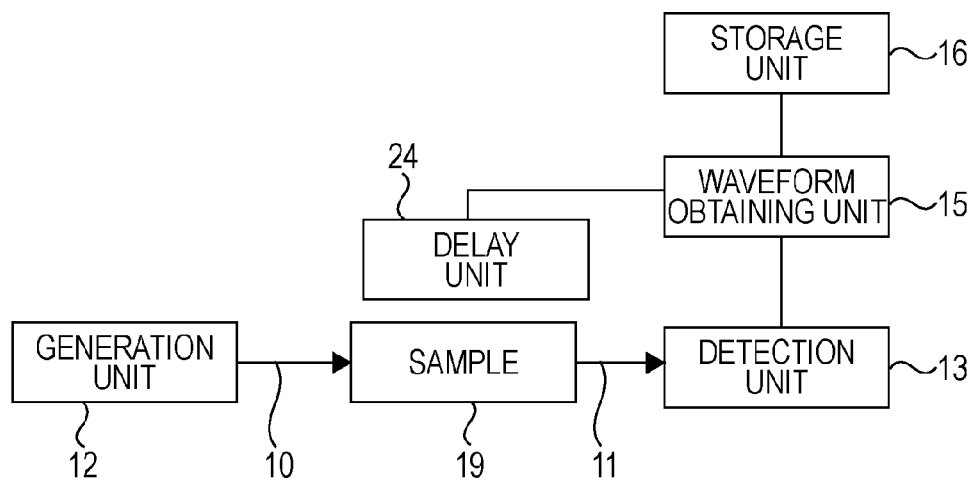

An apparatus according to the embodiments of the present invention will be described with reference to FIGS. 17A and 17B. Herein, FIGS. 17A and 17B illustrate an apparatus for obtaining information related to terahertz waves transmitted through a sample. It is noted that the present invention is not limited to reflection, but as in this first embodiment or as illustrated in FIG. 1, an apparatus for obtaining information related to transmitted terahertz waves may also be used.

A generation unit 12 is configured to generate terahertz waves. Then, a detection unit 13 is configured to detect terahertz waves 11 transmitted through a sample 19, which is originated from terahertz waves 10 generated by the generation unit 12. It is noted that details of the generation unit 12 and the detection unit 13 in the first embodiment are described below.

A delay unit 14 is configured to change a timing at which the detection unit 13 performs the detection. As illustrated in FIG. 17A, in order to control the distance over which the generated terahertz waves 10 to propagate, the delay unit 14 can be configured to change the distance between the generation unit 12 and the detection unit 13. For example, a stage for moving the generation unit 12 is provided, and by changing the distance between the generation unit 12 and the detection unit 13 while moving the stage, it is possible to change the distance over which the terahertz waves 10 propagates.

Herein, as in a delay unit 24 of FIG. 17B, it is also possible to control the propagation speed of the generated terahertz waves 10, this being done by adopting a configuration such that the refractive index of the propagating region can be changed. For example, by locating a member (a dielectric or the like) having a tropism closer to the terahertz wave transmitted through the sample, it is possible to change the refractive index of the propagating region.

With these configurations, it is possible to retard the time at which the terahertz waves reaches the detection unit 13.

In addition, as will be described later, the delay unit can also be configured by changing the timing of generation of the terahertz waves and the time of detection of the terahertz waves, or both. As an example of this configuration, a mirror which moves in an optical axis direction for optical delay is provided (equivalent to a delay optical unit 104 in FIG. 1). At this time, a laser unit arranged to irradiate the generation unit 12 and the detection unit 13 with laser light (which is denoted by reference numeral 101 in FIG. 1) is used. Also, a beam splitter for splitting the laser light is used. The laser beams resulting from splitting by the beam splitter are respectively irradiated to the generation unit 12 and the detection unit 13. The laser beam directed to the detection unit 13 is transmitted through the delay unit (the mirror moving in the optical axis direction).

Furthermore, the delay unit can also be configured to effect an electrical delay. For example, the configuration can be realized by retarding the time of a signal generated for mixing with the detected terahertz wave signal.

A storage unit 16 is configured to pre-store information related to the sample 19. Herein, the information related to the sample 19 pre-stored by the storage unit 16 is preferably a previously obtained temporal waveform of terahertz waves transmitted through the sample. The terahertz waves used to produce this information would preferably have the same characteristics as does that used in the apparatus of the invention. Also, the information related to the sample 19 includes, for example, the size (thickness) of the sample, the refractive index, the transmittance, the reflectivity, the absorbency index, etc. Furthermore, certain physical properties of the sample 19, such as the crystal structure, the composition, and the like, such as the water content, which can be derived from the above-described information, may be used. It is noted that the present invention is not limited to the above-described information, however, and further specific description will be provided below.

A waveform obtaining unit 15 (equivalent to a processing unit 107 in FIG. 1) is configured to obtain the temporal waveform of the terahertz waves by using the delay unit 104. Herein, the waveform obtaining unit 15 samples the terahertz waves detected by the detection unit 13 on the basis of the timing changed by the delay units 14 and 24, and it is thus possible to obtain the temporal waveform of the transmitted terahertz waves.

The delay units 14 and 24 are controlled so that the detection unit 13 detects the terahertz waves in the region related to the temporal waveform which is set on the basis of the information related to the sample 19 pre-stored in the storage unit 16. The control may be carried out by the waveform obtaining unit 15. Then, it is possible to obtain the temporal waveform of the transmitted terahertz waves in the region. With this configuration, it is possible to obtain the information related to the sample 19. Also, by obtaining the temporal waveform in the area, it is possible to shorten the period of time for obtaining the information related to the sample 19 as compared with a procedure in which one obtains all regions of the temporal waveform.

Figure 2:
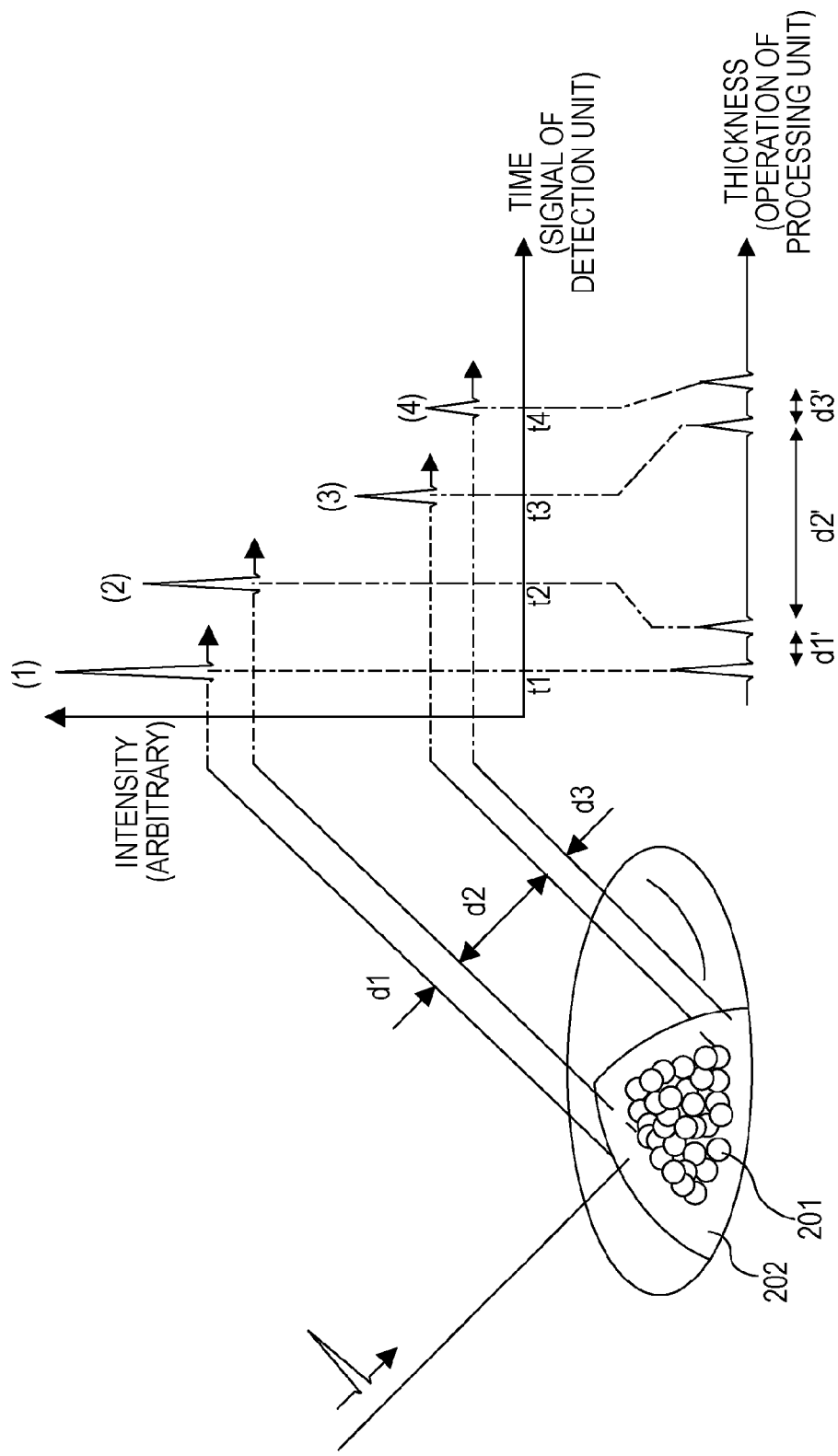
FIG. 2 is an explanatory diagram for describing an operation for obtaining internal information on a tablet as an example.

Herein, the region related to the temporal waveform may, for example, be the pulse of the temporal waveform is conceivable (for example, (1), (2), (3), and (4) in FIG. 2). Also, as the region related to the temporal waveform, the peak of the pulse can instead be used. Furthermore, a part having a large absolute value of the pulse gradient or the like is also usable this purpose.

The pulse is a characteristic area of the temporal waveform of the transmitted terahertz waves. Therefore, by obtaining the pulse, it is possible to find information related to the sample. For example, from the intervals between the pulses, it is possible to derive the thickness the sample 19. It is noted that the "characteristic area" is not limited to the pulse, and an arbitrary area may be used, chosen from various portions of the temporal waveform of the transmitted terahertz waves.

(Obtaining Information Related to Sample or State of Sample)

From the temporal waveform of the transmitted terahertz waves in the region, it is possible to obtain information related to the sample. The information related to the sample is, for example, the size (thickness) of the sample, the refractive index, the transmissivity, the reflectivity, the absorbency index, etc. From the above-described information, it is possible to derive the physical properties of the sample, the crystal structure, the composition, and the like, for example, the water content.

In addition, the temporal waveform of the transmitted terahertz waves in the region (or the pulse of the temporal waveform of the transmitted terahertz waves in the region) is preferably compared with the information pre-stored in the storage unit (for example, the pulse of the previously obtained temporal waveform of the terahertz waves transmitted through the sample). With this configuration, it is possible to derive the state of the sample.

Herein, the "state of the sample" being referred to is particularly a difference between the physical properties of the sample, the crystal structure, the composition, and the like, and the previously obtained information (the pulse of the temporal waveform, or the like).

It is noted that the information related to the sample and the state of the sample are not limited to the above-described information and state, as described below.

(Accumulation Processing while Counting Measurement Times)

It is preferable that the number of times to measure the sample is counted, the measured terahertz waves detected by the detection unit are accumulated, and the accumulation value and the measurement times are used to obtain an average intensity of the terahertz waves. These details will be described with reference to a sixth embodiment, below.

(Fiber Laser)

It is preferred to provide a fiber laser for generating a pulse laser. An optical fiber can be used as an oscillation medium of the laser. In addition, the generation unit is preferably a photoconductive element for generating the terahertz waves by means of operation (lasing) of the pulse laser. Furthermore, the detection unit is preferably a photoconductive element for detecting the terahertz waves through the irradiation of the pulse laser. For the photoconductive element, low-temperature growth GaAs or InGaAs can be used.

Details of the fiber laser will be described with reference to a seventh embodiment, below.

(Method of Obtaining Information Related to Terahertz Wave)

A method of obtaining information related to the terahertz waves transmitted through or reflected by the sample according to another embodiment of the present invention will now be described.

First, the terahertz waves are generated.

Next, terahertz waves transmitted or reflected by a sample, which are originated from the generated terahertz waves, are detected. Herein, the reflected terahertz waves are preferably a pulse reflected by a refractive index boundary face of the sample coated with a coating film. It is noted that a detail of the coating film will be described in the first embodiment, FIG. 2, and the like.

Also, by changing the detection timing, the temporal waveform of the terahertz waves is obtained.

In addition, the region related to the temporal waveform is set on the basis of the previously obtained temporal waveform of the terahertz waves transmitted through or reflected by the sample. Then, the timing is changed so that the transmitted terahertz waves are detected in the area. With this configuration, it is possible to obtain the temporal waveform of the transmitted terahertz waves in this region.

Herein, it is possible to obtain the information related to the sample from the temporal waveform of the transmitted terahertz waves in the region. The information related to the sample is, for example, the size (thickness) of the sample, the refractive index, the transmissivity, the reflectivity, the absorbency index, or the like. From the above-described information, it is possible to derive the physical properties of the sample, the crystal structure, the composition, and the like, for example, the water content.

In addition, the temporal waveform of the transmitted terahertz waves in the region (or the pulse of the temporal waveform of the transmitted terahertz waves in the region) is preferably compared with the pulse of the previously obtained temporal waveform of the terahertz waves transmitted through the sample. With this configuration, it is possible to derive the state of the sample.

Herein, the "state of the sample" being discussed is particularly a difference between the physical properties of the sample, the crystal structure, the composition, and the like, and the previously obtained information (the pulse of the temporal waveform, or the like). It is noted that the information related to the sample and the state of the sample are not limited to the above-described information and state, and details thereof will be further described in the first embodiment.

According to the embodiments of the present invention, a sample the internal information of which can be estimated is set as a target. Then, this internal information is set as standard information and regarded as a measurement reference. For example, a reference is made to the measurement reference based on this standard information, and a measurement area in a depth direction of the sample (for example, in the vicinity of the refractive index boundary face, an area where contamination is easily generated, a material having a desired physical property, or the like) is selected. The measurement is carried out only in this selected area, and the standard information regarding the measurement part is updated, so that the reconstruction is performed.

According to the embodiments of the present invention, on the basis of these measurement results and the standard information in the selected measurement area, it is also possible to reconstruct a time response waveform. By using this response waveform, a spectrographic analysis of the sample or imaging is carried out. Also, by comparing this response waveform with the standard information of the sample functioning as the reference, screening of the sample and adjustment of the apparatus are carried out.

Hereinafter, more specific embodiments will be described with reference to the drawings.

EMBODIMENTS

First Embodiment

Reflection Type

The present embodiment represents a configuration example of the terahertz wave detection apparatus according to the present invention. FIG. 1 illustrates a configuration example of the terahertz wave detection apparatus according to the present invention. As illustrated in FIG. 1, the terahertz wave detection apparatus according to the present embodiment is composed of a laser unit 101, a generation unit 102, a detection unit 103, the delay optical unit 104, a delay time adjustment unit 105, an information storage unit 106, and the processing unit 107. Also, FIG. 1 illustrates a mode in which a sample 109 is conveyed by a conveyance unit 108. It is noted that the sample 109 does not necessarily have to be conveyed for application of the invention.

The laser unit 101 is a part for driving the generation unit 102 and the detection unit 103 by means of laser light. Hereinafter, laser light for driving the generation unit 102 may be referred to as "pump light", and laser light for driving the detection unit 103 may be referred to as the "probe light" in some cases. According to the present embodiment, the laser unit 101 uses a titanium-sapphire laser having a pulse width of 50 fsec, a center wavelength of 800 nm, and a cyclic frequency of 76 MHz.

The generation unit 102 is a part for generating the terahertz waves through the pump light incoming from the laser unit 101. According to the present embodiment, as the generation unit 102, a photoconductive element having an antenna pattern formed on a semiconductor thin film is used. To be specific, as the semiconductor thin film, low-temperature growth GaAs (LT-GaAs) formed through molecular-beam low-temperature epitaxial growth (250° C.) is used for a semi-insulating gallium arsenide (SI-GaAs) substrate (specific resistance $>1\times10^7$ $\Omega\cdot$cm). Then, a dipole antenna made of gold (Au) (the antenna length of 30 μm, the conductor width of 10 μm) having a gap of 5 μm at the center is formed on LT-GaAs. To generate the terahertz waves, in a state where this gap is applied with a bias of 10 V, the pump light is irradiated. As a result, pulsed terahertz waves having a half-bandwidth of about 200 fsec are generated. It is noted that the antenna shape is not limited to the shape just described. For example, a bow-tie antenna or a spiral antenna, which is a common wideband antenna, may also be used. Also, the semiconductor thin film is not limited to the above configuration, and, for example, a semiconductor material such as indium gallium arsenide (InGaAs) may also be used. Also, the semiconductor material itself may also be used for the generation unit 102. For example, a mirror polished GaAs surface is irradiated with the pump light, and the terahertz waves are generated through the time change of a momentary current generated at this time. Also, an organic crystal such as DAST (4-dimethylamino-N-methyl-4-stilbazolium tosylate) crystal may also be used.

The detection unit 103 is a part for detecting the terahertz waves through the probe light incoming from the laser unit 101. In the detection unit 103, at the timing of incidence of the terahertz waves, the probe light is irradiated, and the resulting generated current is detected. With this configuration, the terahertz waves are obtained. For the detection unit 103, the photoconductive element or the like having the antenna pattern on the semiconductor thin film similarly to the generation unit 102 is used.

The delay optical unit 104 is a part for optically adjusting the delay interval of the probe light with respect to the pump light (the delay time). While changing the delay time, the terahertz waves detected by the detection unit 103 are measured, thus performing so-called terahertz time domain spectroscopy (THz-TDS). While changing the delay time, the response of the terahertz waves obtained from the detection unit 103 for every delay interval is plotted by the processing unit 107, so that it is possible to obtain the time response of the terahertz waves. In FIG. 1, for simplicity, illustrations of a chopper and the like necessary to the THz-TDS are omitted. According to the present embodiment, as illustrated in FIG. 1, a reflection type optical system is provided to the sample 109.

According to the present embodiment, it is characteristic that the delay time adjustment unit 105 and the information storage unit 106 are further provided to this THz-TDS.

The information storage unit 106 is a part for pre-storing the internal information of the sample 109 as the standard information. For example, the position of the refractive index boundary face related to the internal part of the sample 109 and the response waveform of the terahertz wave are stored. The information stored therein is obtained from a specification at the time of manufacturing the sample 109. Also, the sample which becomes the standard and the time response waveform of the sample arbitrarily selected from among the sample group are measured in advance (this measurement(s) may also be referred to herein as "previous measurement"), and this measurement result may be set as the standard information. For example, the position of the refractive index boundary face is found from the reflected waveform of this temporal response waveform to obtain the physical properties.

The delay time adjustment unit 105 is a part for controlling the delay optical unit 104. Herein, reference is made to the standard information on the internal part of the sample stored in the information storage unit 106, and in order to detect the terahertz waves from a predetermined measurement area in the depth direction such as the refractive index boundary face, the delay time of the probe light is adjusted. In a case where the measurement area to be desired to be detected exists in a discontinuous manner, the delay time of the probe light is changed in a discontinuous manner. Then, by continuously changing the delay time only in the measurement area existing in a discontinuous manner, the terahertz waves related to the measurement area are detected. That is, a time when the terahertz waves reach the detection unit 103 is predicted on a basis of the known internal information for the sample, and an adjustment is carried out on the delay time of the probe light for operating the detection unit 103.

In this manner, the signal of the terahertz waves obtained from the detection unit 103 partially loses a concept of the time axis as the delay optical unit 104 is changed in a discontinuous manner (FIG. 2, the signal of the detection unit). For example, as illustrated in FIG. 2, the delay time of the delay optical unit 104 is selected by the delay time adjustment unit in a discontinuous manner like t1→t2→t3→t4, and responses (1), (2), (3), and (4) of the terahertz waves in the respective delay times are obtained. For that reason, time information between the measurement areas is missing. According to the present embodiment, in order to compensate for this missing part, the processing unit 107 is used. For example, in the processing unit 107, a reference is made to the adjustment amount of the delay time carried out by the delay time adjustment unit 105, and the response of the terahertz waves obtained by the detection unit 103 is reconstructed into the actual time response of the terahertz waves (FIG. 2, the operation of the processing unit). To more be specific, time intervals of the responses (1), (2), (3), and (4) of the terahertz waves in the respective delay times are adjusted, and the response of the terahertz waves corresponding to the internal information on the sample is obtained.

The operation of the terahertz wave apparatus will be described. In FIG. 1, the terahertz wave pulse generated from the generation unit 102 is irradiated to the sample 109. The structure of the sample 109 at this time is supposed to be the structure in FIG. 2. It is noted that for the sake of the operation description, herein, the structure of the sample 109 is described while supposing that the thickness of a coating film 202 is set as 300 μm (d1 and d3), and the thickness of a fine particle 201 is set as 3 mm (d2). Also, for the simplification of the operation description, the refractive index of the respective materials is supposed to be 1, and the wavelength shortening effect due to the refractive index of these materials (the propagation length) thus need not be taken into account. The terahertz waves incident on the sample 109 are reflected, for example, by the refractive index boundary face existing in the sample 109. In the sample 109 of FIG. 2, the terahertz waves are reflected by the surface of the coating film 202 structuring the sample 109, the coating film 202, and the refractive index boundary face of the fine particle 201. These reflected waves are incident on the detection unit 103 with a time difference in accordance with the reflected position of the terahertz waves. In FIG. 1, a reflected pulse from the surface of the coating film 202 is denoted as (1), and a reflected pulse from a boundary face between the coating film 202 and the fine particle 201 is denoted as (2). Herein, for simplifying the description, a reflected pulse (3) from a boundary face between the coating film 202 and the fine particle 201 and a reflected pulse (4) from a boundary face between the coating film 202 and the outside are omitted. As described above, when it is supposed that the film thickness of the coating film 202 is set as 300 μm, the time difference between the reflected pulses (1) and (2) is about 2 picoseconds (psec).

In the information storage unit 106, the information related to the internal part of the sample 109 is pre-stored as the standard information. As described above, this standard information is obtained from a specification at the time of manufacturing the sample or a previous measurement of an arbitrarily selected sample. For example, positions on the time axis where the reflected pulse (1) and the reflected pulse (2) are generated, and the intensity, the pulse width, and the like of the respective reflected pulses are stored. For example, in a case where the positions on the time axis where the reflected pulses are generated are stored in the information storage unit 106, the following setting is established. It is noted that the position of the reflected pulse (1) varies depending on the measurement system of the apparatus, but herein, 5 psec is supposed.

The reflected pulse (1) . . . t1=5 psec
The reflected pulse (2) . . . t2=7 psec
The reflected pulse (3) . . . t3=27 psec
The reflected pulse (4) . . . t4=29 psec Then, the positions on the time axis for the respective pulses are used as the measurement reference for deciding the delay time of the delay time adjustment unit 105. Also, as will be described later, in a case where the present apparatus is used for the screening of the sample 109 these pieces of the standard information may also be used as information for the comparison.

According to the THz-TDS in the related art, the response waveforms from the reflected pulse (1) to the reflected pulse (4) are continuously obtained. However, according to the present embodiment, the delay time adjustment unit 105 makes a reference to the time interval between the reflected pulses (1) and (2) stored in the information storage unit 106 as the standard information to control the delay optical unit 104. For example, in the case where the time interval between the reflected pulses (1) and (2) is 2 psec, the delay optical unit 104 adjusts the optical length by 0.6 mm. Similarly, in the case of the time interval between the reflected pulses (2) and (3), the delay optical unit 104 adjusts the optical length by 6.0 mm, and in the case of the time interval between the reflected pulses (3) and (4), the delay optical unit 104 adjusts the optical length by 0.6 mm.

For example, first, the delay time adjustment unit 105 refers to the measurement reference obtained from the standard information which is stored in the information storage unit 106, to obtain the delay time generated by the reflected pulse (1). In this example, the delay time adjustment unit 105 obtains 5 psec from the information storage unit 106 as the delay time of the reflected pulse (1). Then, the delay time adjustment unit 105 changes the distance through which the probe light passes in reaching the detection unit 103, by moving the delay optical unit 104, and a desired delay time is provided to the apparatus. At this measurement position, in order to measure the reflected pulse (1), the delay optical unit 104 continuously changes the delay time of the probe light. For example, in a case where a waveform having the pulse width of 1 psec is desired to be obtained, the delay optical unit 104 is moved by about 0.3 mm. It is noted that the term "continuously" herein means that the delay optical unit 104 is moved by a target distance in a predetermined interval. For example, when the predetermined interval is set as 100 µm, the delay optical unit 104 is moved at a constant speed until the delay optical unit 104 has been moved by 0.3 mm. The processing unit 107 plots the signal of the detection unit 103 with respect to the delay time which continuously changes, and the response waveform equivalent to the reflected pulse (1) is obtained.

After that, the delay time adjustment unit 105 refers to the measurement reference obtained from the standard information which is stored in the information storage unit 106, and obtains the delay time generated by the reflected pulse (2).

Herein, the delay time adjustment unit 105 obtains 7 psec from the information storage unit 106 as the delay time of the reflected pulse (2). Then, the delay time adjustment unit 105 moves the delay optical unit 104 by 0.6 mm so as to obtain the delay time when the reflected pulse (2) is generated again, and the measurement operation of the reflected pulse (2) is started.

Figure 15A:
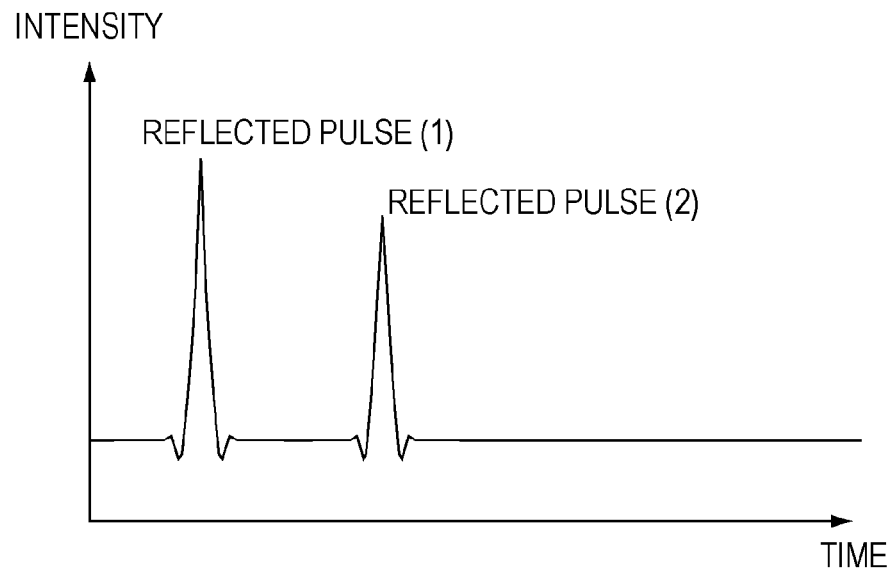
FIGS. 15A and 15B are explanatory diagrams for describing an operation of the apparatus according to the first embodiment of the present invention.
Figure 15B:
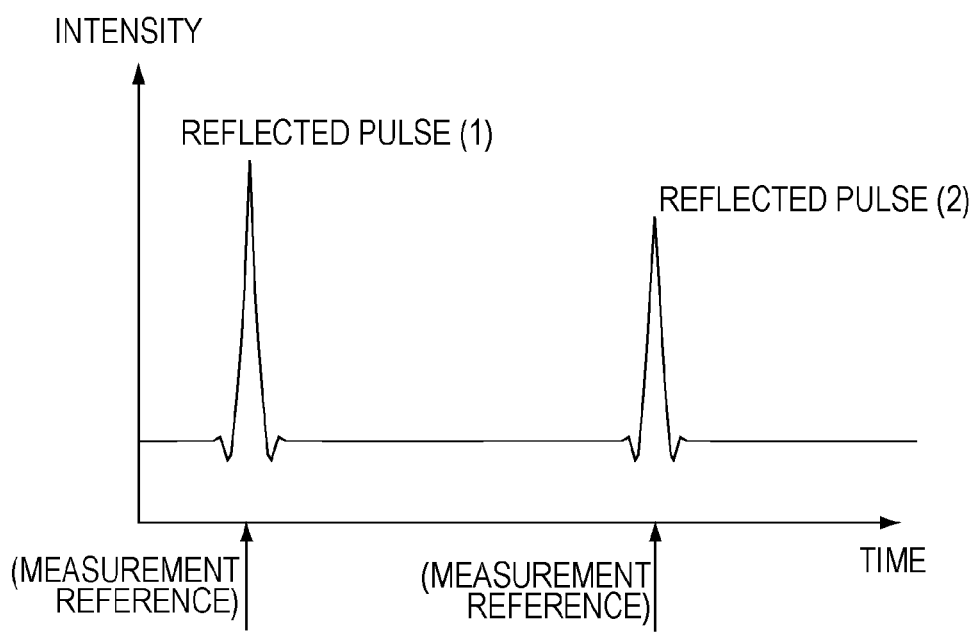

In this manner, the present embodiment includes a step of adjusting the delay optical unit 104 by the delay time adjustment unit 105 in a discontinuous manner. The response waveform of the terahertz waves obtained in the processing unit 107 has a temporal waveform where the reflected pulses (1) and (2) continuously appear as illustrated in FIG. 15A. As described above, this response waveform misses information on the pulse interval between the respective pulses. For that reason, as illustrated in FIG. 15B, the processing unit 107 refers to the measurement reference of the delay time carried out by the delay time adjustment unit 105 in a discontinuous manner, and provides the time difference of the respective measurement references to the reflected pulse (1) and the reflected pulse (2), thus reconstructing the response waveform. Herein, a time interval 2 psec corresponding to the movement amount of the delay optical unit 104 is provided between the reflected pulse (1) and the reflected pulse (2).

In this manner, according to the present embodiment, the method of specifying the rough measurement position by the information storage unit 106 and obtaining the response of the terahertz waves only in the predetermined measurement position is used. With this configuration, it is not necessary to measure the terahertz waves continuously over the entire measurement time as in the THz-TDS carried out in the related art, and it is thus easier to shorten the measurement time for the time difference between the respective measurement references.

FIG. 2 is a cross-sectional view and an operation of the sample 109 when a tablet is taken as being the sample 109. As illustrated in FIG. 2, the sample 109 has a form of consolidated fine particles 201 coated with a coating film 202. The fine particles 201 are obtained by consolidating a powdered state medicinal agent mixed with an additive. The coating film 202 includes, for example, saccharose, a water-soluble polymer, an insoluble polymer, etc. Depending on cases, a form without the coating film 202 (uncoated tablet) is also conceivable. According to the present embodiment, a sugar-coated tablet which is obtained by coating a core tablet with sugar is supposed. At this time, thicknesses d1 and d3 of the coating film 202 are often set as several tens of µm to several hundreds of µm, and a thickness d2 of the tablet 109 is often set as several mm. As illustrated in FIG. 2, the terahertz waves irradiated on the sample 109 become the reflected pulse (1) which is reflected by the surface of the coating film 202. Also, the terahertz waves are reflected by the refractive index boundary face such as the reflected pulses (2) and (3) which are reflected by the boundary face between the coating film 202 and the fine particles 201, and then the reflected pulse (4) reflected again by the surface of the coating film 202. In general, in the measurement based on short wavelengths such as visible light or X-rays, it is difficult clearly to distinguish this refractive index boundary face. This is because, in general, the medicinal agent grain diameter is several tens of µm, and the shape of the boundary face is changed in a complex manner while following the grain diameter distribution of the fine particles 201 on the refractive index boundary face. However, the value of the grain diameter is equivalent or sufficiently small as compared with the wavelength of the terahertz waves. In other words, the wavelength of the terahertz waves is moderately large, and the shape of the boundary face is not so clearly detected as compared with the measurement of the short wavelength. In other words, the unclear shape of the boundary face for short wavelengths can be recognized as a relatively clear shape of the boundary face for terahertz waves. Also, the terahertz waves have a moderate transmissivity for the fine particles 201, and thus the terahertz waves are more suitable to obtain information on the boundary face of the fine particles, as compared with a measurement based on short-wavelength radiation like those mentioned above.

According to the present embodiment, these pieces of information on the boundary face are stored in the information storage unit 106, and in the delay time adjustment unit 105, the positions (1), (2), (3), and (4) are selected and subsequently measured. For example, in a case where regarding the respective pulses, a waveform of 2 psec converted on the time axis is to be obtained, a measurement time of total 8 psec is necessary. It is noted that as illustrated in FIG. 2, as the information on the boundary face is sequentially measured, the response detected by the detection unit 103 does not accurately reflect the information on the thickness. According to the present embodiment, the processing unit 107 converts the adjustment amount of the delay time of the probe light adjusted by the delay time adjustment unit 105 to be reflected on the response waveform. As a result, it is possible to measure accurate film thicknesses (d1', d2', and d3').

In a case where the above-described operation is carried out through the THz-TDS in the related art, the measurement time of about several hundreds of psec is necessary. In contrast to this, in the configuration according to the present embodiment, it is possible to obtain the internal information on the sugar coated tablet (sample) in a measurement time of several psec as such a configuration is used that the rough measurement position is specified and only the waveform response at the measurement position is obtained to carry out the reconstruction. For that reason, as compared with the method in the related art, the measurement at a higher speed is facilitated.

It is noted that according to the present embodiment, the film thickness in the depth direction of the sample 109 has been described, but the present invention is not limited to the above. As illustrated in the THz-TDS in the related art, by using the intensity and the delay information on the terahertz waves at the selected measurement position, it is also possible to measure the change of the physical properties, the difference of the crystal structures, the blend ratio, the composition, the density of the fine particles, a material having a desired physicality, and the like. For example, as a method of obtaining the physical properties, the complex refractive index is obtained from the intensity of the reflection pulse and the delay time, and the desired physical property is converted therefrom. It is also possible to adopt a mode of measuring this change of the physical property. Moreover, by verifying the difference of the fingerprint spectra in the terahertz region, it is also possible to determine a difference in crystal structures. Furthermore, the fingerprint spectrum obtained is supposed to be composed of the fingerprint spectrum related to a plurality of substances, and it is also possible to predict the blend ratio from a computation for separating the spectra or the intensity or spread of the respective spectra. Alternatively, such a mode may also be adopted that the determination is carried out while the analytical curve of the respective spectra which follow the thickness or concentration of the sample is used. On the basis of the transmissivity, the reflectivity, or the spectrum information related to these, the density of the fine particles can also be verified. In a similar manner, the verification of the composition for finding out which molecules an aggregation of the substance is made of can also be carried out. These methods are appropriately combined and selected while following purposes.

It is noted that according to the present embodiment, the tablet is exemplified as the sample 109, but the present invention is not limited to the above. Generally, it should be considered that any sample with which internal information of a material can be efficiently obtained may be used.

Second Embodiment

Transmission Type

The present embodiment illustrates a mode related to the terahertz wave detection apparatus according to the present embodiment. To more be specific, the present embodiment illustrates a modified example of the terahertz wave detection apparatus according to the first embodiment. It is noted that that part of the description which is common to this embodiment and the above-described embodiment will be omitted.

Figure 3:
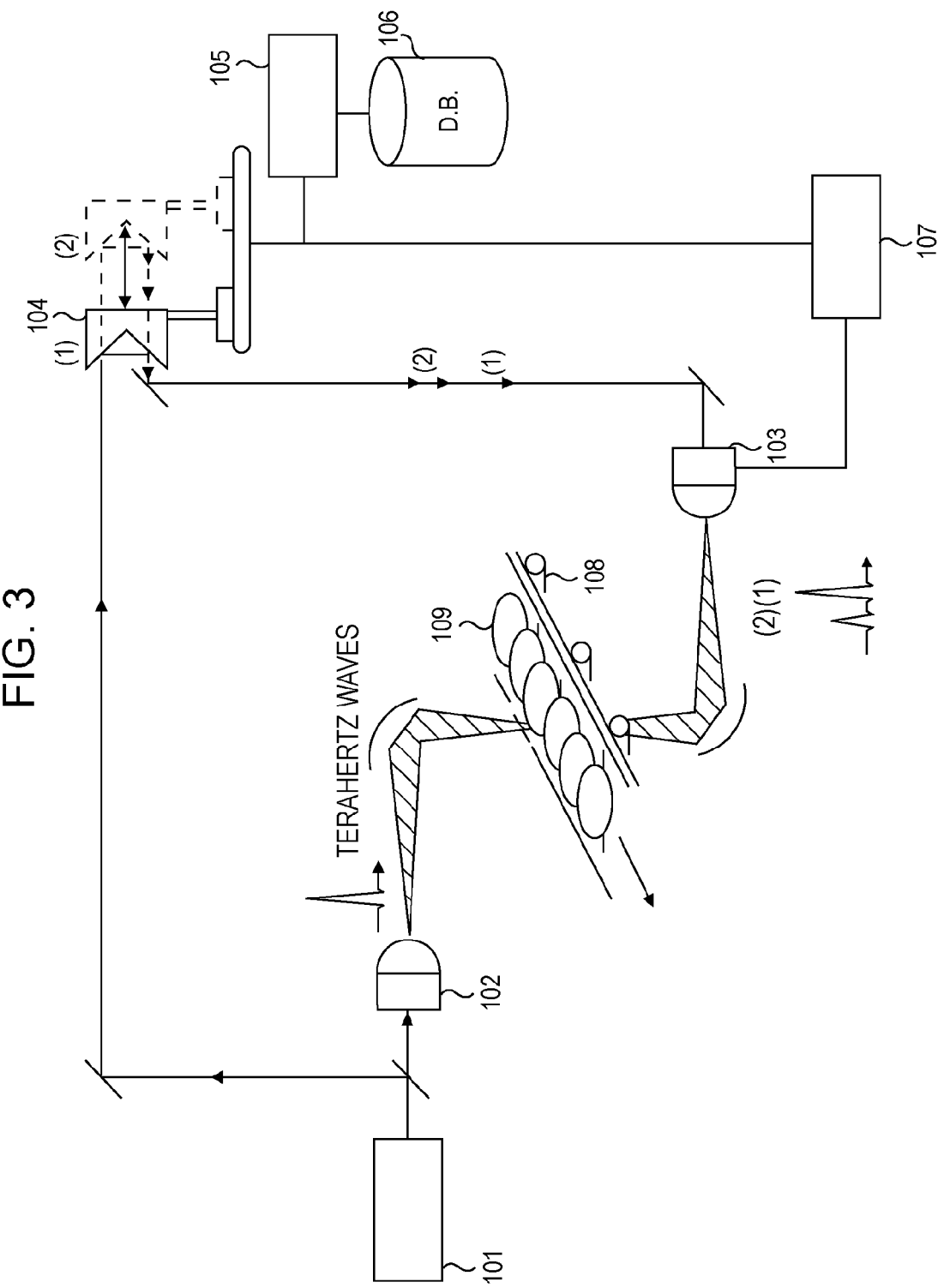
FIG. 3 is a schematic configuration diagram of an apparatus according to a second embodiment of the present invention.

FIG. 3 illustrates a modified example of the terahertz wave detection apparatus according to the present embodiment. As illustrated in FIG. 3, in the terahertz wave detection apparatus according to the present embodiment, the propagation path of the terahertz waves has a transmission type optical arrangement with respect to the sample 109.

The operation of the terahertz wave detection apparatus according to the present embodiment will be described. It is noted that in the description of the operation, a description on a common part will be omitted. Herein, the sample 109 is supposed to be the same as that of the first embodiment. That is, for the structure of the sample 109, it is supposed that the thickness of the coating film 202 is 300 µm, and the thickness of the fine particle 201 is 3 mm. Also, the refractive index of the respective materials is supposed to be 1 for simplifying the operation description, and the wavelength shortening effect due to the refractive index of these materials (the propagation length) is not taken into account. Herein, the transmitted pulse detected by the detection unit 103 is supposed to be the transmitted pulse illustrated in FIG. 16. As illustrated in FIG. 16, a transmitted pulse (1) is a pulse transmitted through the sample 109. A transmitted pulse (2) and the transmitted pulse (3) are pulses reflected by the surface of the coating film 202 and reflected by the boundary face between the coating film 202 and the fine particle 201 once. A transmitted pulse (4) is a pulse reflected between the surfaces of the coating film 202 once.

For example, the information storage unit 106 stores positions on the time axis where these transmitted pulses are generated. It is noted that pulses other than the above-described transmitted pulses also exist. For example, such pulses include a transmitted pulse reflected by the boundary face twice or a transmitted pulse reflected by a boundary face different from the above-described boundary face, etc. The detection unit 103 detects, in addition to the transmitted pulse necessary to the inspection, these pulses mixed on the time axis in enumeration. According to the present embodiment, the positions on the time axis pre-stored in the information storage unit 106 are limited, and it is thus possible to carry out the inspection while filtering the pulses which are not used for the inspection. Therefore, inspection efficiency is increased.

According to the present embodiment, the positions on the time axis of the transmitted pulse are set as follows. It is noted that the position of the transmitted pulse (1) changes due to the setting of the measurement system of the apparatus, but herein, 5 psec is supposed.

The transmitted pulse (1) ... t1=5 psec
The transmitted pulse (2) ... t2=7 psec
The transmitted pulse (3) ... t3=27 psec
The transmitted pulse (4) ... t4=29 psec The position of the respective transmitted pulse on the time axis are used as the measurement reference for deciding the delay time of the delay time adjustment unit 105. The adjustment amounts of the delay optical unit 104 with respect to these delay times are as follows.

From the transmitted pulse (1) to the transmitted pulse (2) ... 0.6 mm

From the transmitted pulse (2) to the transmitted pulse (3) ... 6.0 mm

From the transmitted pulse (3) to the transmitted pulse (4) ... 0.6 mm

By adopting such an optical arrangement, the terahertz waves have a mode to be transmitted through the internal part of the sample 109. For that reason, the terahertz waves propagating through the sample 109 have a response which reflects the rough characteristic features in the depth direction of the sample 109. For example, when the medicinal agent illustrated in FIG. 2 is supposed as the sample 109, from the absorbance index the first transmitted pulse (1), it is possible to estimate the density of the entire sample 109, the absorbed amount of the terahertz wave, the composition, and the like. Also, by monitoring the phase shift amount (or the time delay amount), the thickness of the entire sample 109 can be estimated.

In this manner, by adopting the transmission type arrangement, it is possible to easily estimate the overall characteristic features of the object to be measured.

Third Embodiment

Comparison Unit

Figure 4:
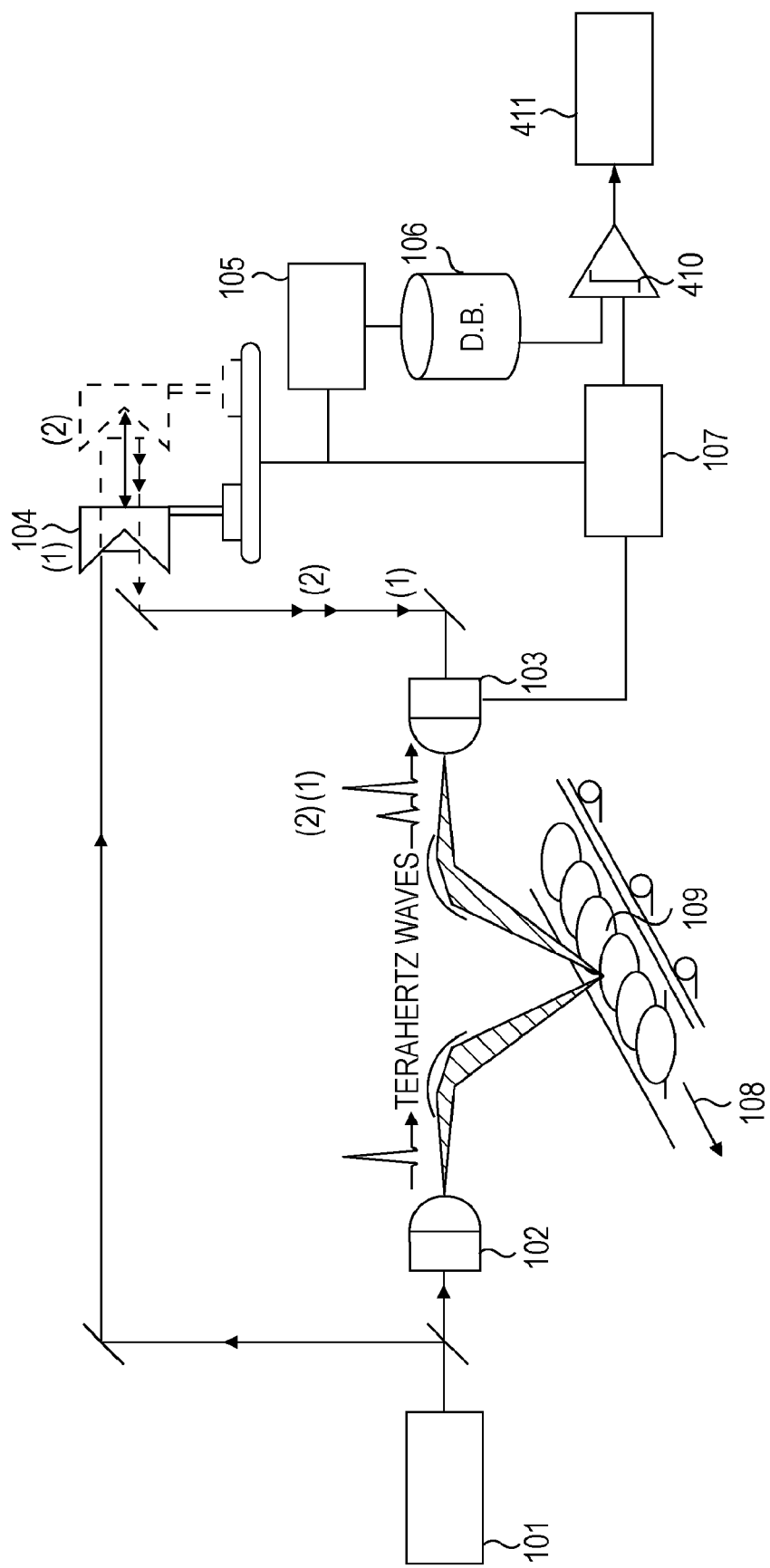
FIG. 4 is a schematic configuration diagram of an apparatus according to a third embodiment of the present invention.

FIG. 4 illustrates a mode related to an inspection system according to the present invention. As illustrated in FIG. 4, the inspection system according to the present embodiment has a configuration in which a comparison unit 410 and an apparatus control unit 411 are added to the configuration of the terahertz wave detection apparatus according to the first embodiment. Description of parts common to this embodiment and to the first embodiment will be omitted.

The comparison unit 410 refers to the internal information of the sample 109 obtained by the processing unit 107 and the internal information which becomes the standard of the sample 109 previously stored in the information storage unit 106. Then, a difference between the signal of the processing unit 107 obtained through the actual measurement and the information in the information storage unit 106 is monitored to determine whether the sample 109 in the desired state is obtained.

For example, in a case where the sugar-coated tablet is supposed as the sample 109, the information storage unit 106 stores the thickness of the sugar-coated tablet and the information on the boundary face between the coating film and the tablet (the thickness, and the like). This information is obtained from the manufacturing condition for the sample 109. Also, the sample 109 which becomes a reference is selected, and the measurement data on the terahertz waves with respect to the sample 109 may be used as the internal information which becomes the standard. In the comparison unit 410, a permissible range of an error is set with respect to this information in the information storage unit 106. In a case where the comparison unit 410 carries out the monitoring on the coating film thickness of the sample 109, the permissible error range of the coating film thickness is set in a range where a desired amount of medicinal properties reach a target affected area. It is noted that according to the present embodiment, this permissible error range is set by the comparison unit 410, but the setting position is not limited to the above. For example, in the information storage unit 106, a mode of providing this permissible error range together with the information on the sample 109 may also be adopted.

Also, according to the present embodiment, the information to be compared does not necessarily have to be the response waveform of the terahertz wave. For example, only the intensity of the terahertz waves in the predetermined measurement area can be set as the comparison target too. Also, it is possible to adopt a mode of monitoring whether the intensity at the measurement position falls within the set permissible error range. To more be specific, this mode is to measure the signal intensity at the apex of the respective pulses in FIG. 2. From the change in the signal intensity at the measurement position, the temporal position of the response waveform of the terahertz waves is estimated. In this manner, a mode for setting only the intensity at the measurement position as the measurement and inspection target can also be applied to the above-described embodiments.

As illustrated in FIG. 4, according to the present embodiment, the plurality of samples 109 are provided, and the respective samples are sequentially conveyed by the conveyance unit 108. In the comparison unit 410, with respective to the samples 109, the measurement data of the sample 109 obtained by the processing unit 107 is compared with the information in the information storage unit 106 which becomes the standard to monitor whether the measurement data falls within the permissible error range. Then, the comparison unit 410 determines the sample 109 indicating a characteristic feature out of this permissible error range as a defective product. The apparatus control unit 411 is a part for controlling the apparatus in response to the comparison result of the comparison unit 410. For example, in the case of screening the samples 109 conveyed by the conveyance unit 108, the control is carried out so as to remove the sample 109 identified as a defective product. The sample 109 to be removed may be only the sample 109 that has been identified as itself being defective, or may be a group neighboring and including the sample 109 that is defective. Also, in response to the result of the comparison unit 410, the apparatus control unit 411 may adopt a mode of feeding the manufacturing condition in the manufacturing step for the sample 109 back to a desired condition. For example, in a case where the sugar-coated tablet is supposed as the sample 109, the film thickness of the coating film is adjusted. Also, in a case where the physical property of the boundary face between the coating film and the tablet exceeds the permissible error as the blend ratio of the medicinal agent to the additive agent changes or the crystal structure of the medicinal agent changes, for example, the adjustment on these manufacturing conditions are carried out.

With such a configuration, it is possible to inspect the inside of the object to be measured in a nondestructive manner. Also, similarly to the first embodiment, such a mode is adopted that reference is made to the information about the inside of the sample which serves as the reference, and the measurement range is limited. Then, the response of the terahertz waves is reconstructed, so that high speed measurement is facilitated. In particular, the mode is preferably used for the inspection system for the medicinal agent.

Also, according to the present embodiment, the inspection part due to the terahertz waves has the reflection type configuration, but the configuration is not limited to the above.

For example, the inspection part due to the terahertz waves may have the transmission type configuration illustrated in the second embodiment. In this configuration, as described above, it is possible in a simple way to estimate the overall characteristic features of the sample. For that reason, for example, it is also possible to add a first-stage screening function of checking the mixture of a foreign substance or the presence or absence of a crack on the basis of the absorbed amount of the terahertz waves or the phase shift. After that, the internal inspection may be carried out only on the samples in which it is checked that there are no macro-structural defects, and therefore it is possible to carry out the inspection effectively.

Fourth Embodiment

A Plurality of Delay Optical Units

The present embodiment illustrates a modification example related to the above-described terahertz wave detection apparatus. To be specific, the modification example relates to an optical system for obtaining the terahertz waves. It is noted that a part of the description that is common to the above-described embodiment will be omitted.

Figure 5:
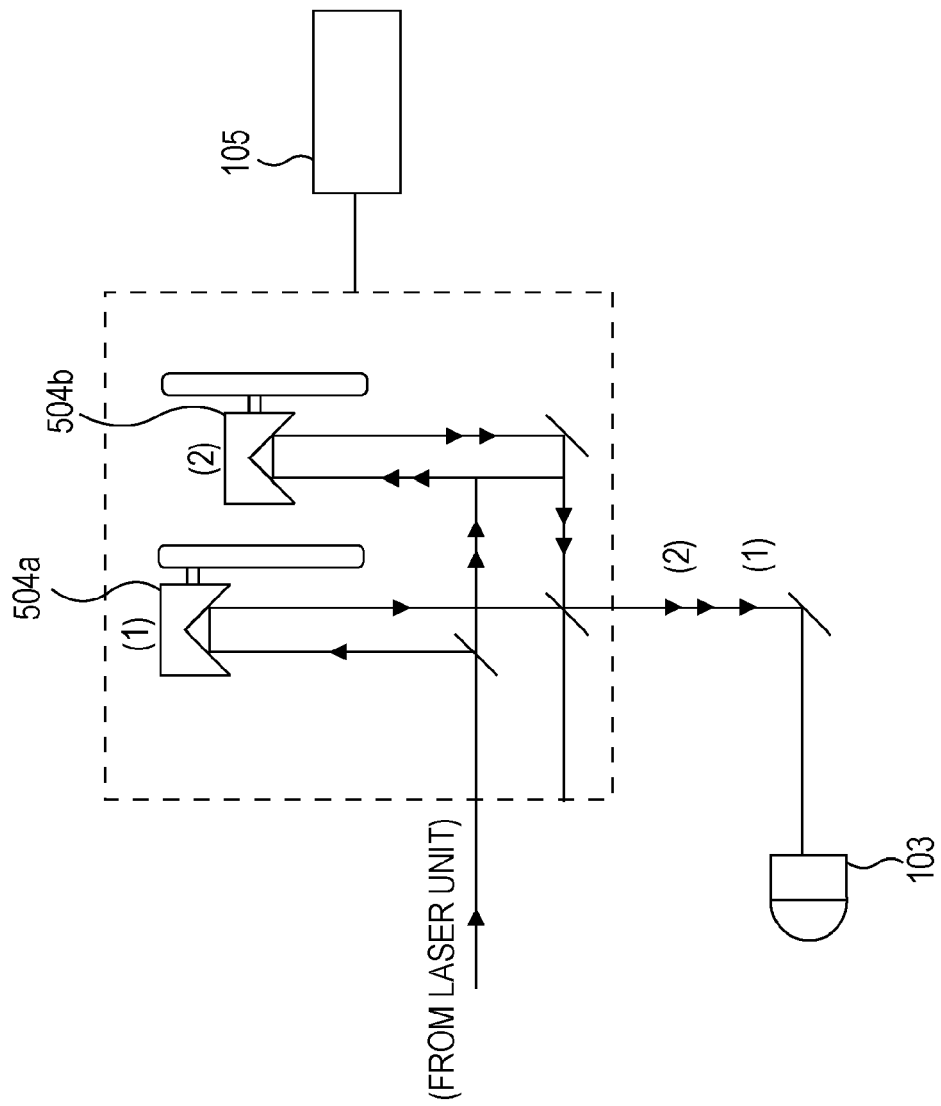
FIG. 5 illustrates a mode example of a delay optical unit of the apparatus according to an embodiment of the present invention.

FIG. 5 relates to the above-described apparatus, illustrating another mode of the delay optical unit 104. As illustrated in FIG. 5, the delay optical unit 104 according to the present embodiment is composed of a plurality of delay optical units 504a and 504b. Then, the respective delay optical units are respectively adjusted to the measurement positions selected by the delay time adjustment unit 105.

For example, as described in the above-described embodiment, such a case is considered that the terahertz waves propagating from the sample 109 have pulses (1) and (2). According to the above-described embodiments, the delay time adjustment unit 105 is used to sequentially move the delay optical unit 104 to the positions corresponding to the respective pulses. According to the present embodiment, as illustrated in FIG. 5, the delay optical unit 504a and the delay optical unit 504b are respectively allocated to the position corresponding to the reflection pulse (1) and the position corresponding to the reflection pulse (2) to measure the response of the terahertz waves.

Herein, the two delay optical units may suffice if the set optical length is ensured, and the positional relation between the two delay optical units is not particularly limited.

It is noted that according to the present embodiment, the respective delay optical units respectively correspond to the respective reflection pulses of the terahertz waves propagating from the sample 109, but the mode is not limited to the above. For example, such a mode may also be adopted that the pulses of the terahertz waves are set as a plurality of reflection pulse groups, and the delay optical units are respectively allocated to the respective reflection pulse groups. In this case, the delay time adjustment unit 105 carries out the operation of setting the measurement positions with respect to the respective reflection pulse groups and sequentially moving the allocated delay optical units.

Figure 10:
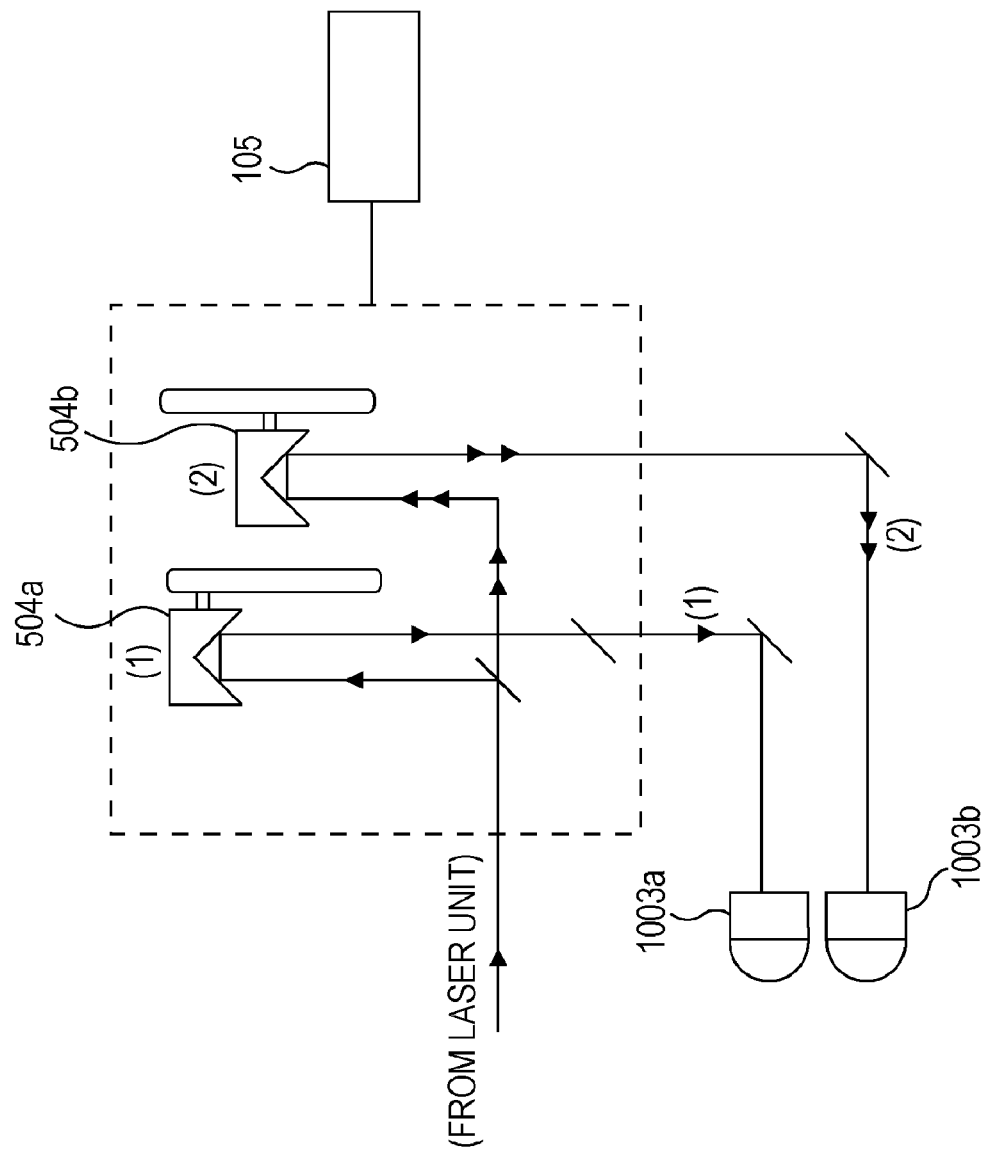
FIG. 10 is a schematic configuration diagram of a part of the apparatus according to the fifth embodiment of the present invention.

In this manner, by using the plurality of delay optical units to be operated in parallel, it is possible to shorten the period of time needed for measuring the response of the terahertz waves. For that reason, it is possible to operate the apparatus according to the embodiment of the present invention at a still higher speed. Also, as illustrated in FIG. 10 it is also possible to such a configuration that the plurality of detection units are allocated to the respective delay optical units. In this case, as compared with the mode of processing through the single detection unit, the standby time for measuring the respective reflection pulses is shortened, and higher-speed operation of the apparatus is facilitated.

Fifth Embodiment

Plurality of Detection Units

The present embodiment illustrates a modified example related to the above-described terahertz wave detection apparatus. To be specific, the modified example relates to the arrangement of the detection unit 103. It is noted that a part of the description common to the above-described embodiment will be omitted.

Figure 9:
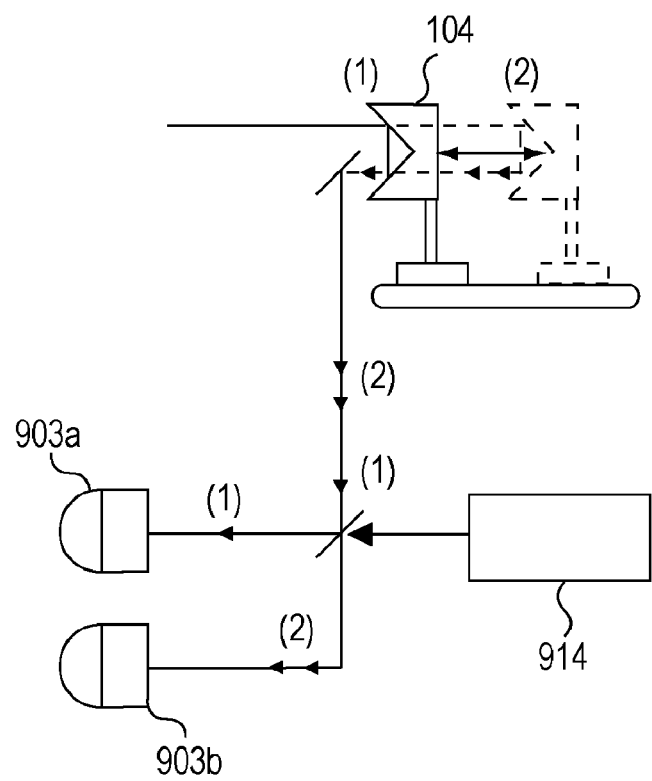
FIG. 9 is a schematic configuration diagram of a part of an apparatus according to a fifth embodiment of the present invention.

FIG. 9 relates to the apparatus described thus far, illustrating another mode of the detection unit 103. As illustrated in FIG. 9, the plurality of detection units 103 according to the present embodiment are provided.

For example, such a case is supposed that depending on a state of the internal part of the sample 109, the propagating directions of the respective pulses of the terahertz wave for propagating the sample 109 are different. To be specific, the propagating directions of the pulses (1) and (2) of the terahertz wave are different from each other. In a case where the plurality of refractive index boundary faces of the sample 109 have different angles with respect to the incidence direction of the terahertz waves, the propagating directions of the pulses (1) and (2) of the terahertz waves are different from each other. For the detection unit 103, an arrangement in which it is possible to obtain the terahertz waves at the highest sensitivity is a configuration of arranging the detection unit 103 in the middle of the propagating path of the terahertz waves. Herein, the arrangement providing the satisfactory sensitivity refers to an arrangement in which the intensity of the terahertz waves detected by the detection unit 103 becomes strongest. When the pulses having different propagating directions exist, for example, a phenomenon may occur in which the sensitivity to pulse (1) is satisfactory, but as to pulse (2), the intensity of the terahertz waves reaching the detection unit 103 becomes small, and the detection sensitivity is decreased. For that reason, a plurality of detection units 903a and 903b are arranged at positions where it is possible to obtain the terahertz waves at the highest sensitivity for the respective pulses. According to the present embodiment, the detection unit 903a is allocated to the pulse (1), and the detection unit 903b is allocated to the pulse (2). Then, while corresponding to the measurement position selected by the delay optical unit 104, by a light path switching unit 914, the probe lights (1) and (2) are respectively allocated to the detection units 903a and 903b. Then, the measurement and the inspection are carried out at the highest sensitivity for the respective pulses.

It is noted that as described in the fourth embodiment, according to the present embodiment, the pulses of the terahertz waves propagating from the sample 109 correspond to the respective detection units, but the present invention is not limited to this mode. For example, for the pulses of the terahertz waves, the pulses having substantially the same propagating direction are set as one pulse group. At this time, the detection units are allocated to the respective pulse groups.

With such a configuration, the detection unit can be optimized to the propagating directions of the respective pulses, and therefore the improvement in the detection sensitivity can be expected. Also, as illustrated in FIG. 10, instead of the light path switching unit 914, such a mode may be used that the plurality of delay optical units described in the fourth embodiment are used. At this time, the respective delay optical units are allocated with pulses in substantially the same propagating direction. In this case, as compared with the mode of processing the single delay optical unit 104, the standby time to measure the respective pulses is decreased, and thus the higher speed of the apparatus is facilitated.

Sixth Embodiment

Accumulation Processing by Counting Measurement Times

The present embodiment illustrates a modified example related to the above-described terahertz wave detection apparatus. To be specific, the modified example relates to a method of obtaining the terahertz wave. It is noted that a part of the description common to the above-described embodiment will be omitted.

Figure 6:
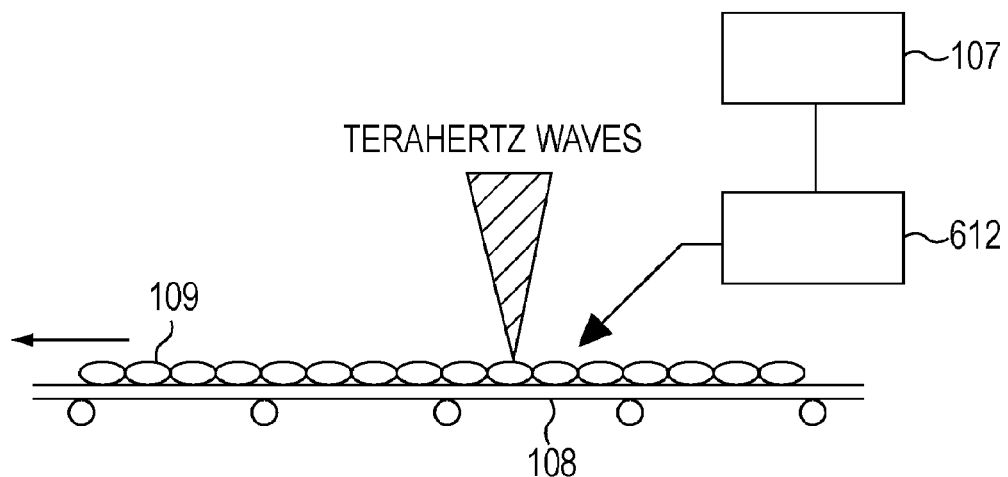
FIG. 6 is a schematic configuration diagram of a part of an apparatus according to a sixth embodiment of the present invention.

As illustrated in FIG. 6, the apparatus according to the present embodiment has a configuration of being further provided with a counter unit 612 for measuring the number of times to measure the response of the terahertz wave and record the number of times to carry out the measurements. According to the present embodiment, the counter unit 612 sets the number of times to carry out the measurements and counts the number of the samples 109 which are measured up to this number of measurements. According to the configurations described thus far, regarding the sample 109 conveyed by the conveyance unit 108, one measurement is carried out on the one sample 109. If the plurality of samples 109 conveyed by the conveyance unit 108 are the same, the measurement results obtained from the respective samples 109 are substantially the same. According to the present embodiment, the processing unit 107 carries out the accumulation processing on the plurality of measurement results by the number of measurement times to be recorded in the counter unit 612, and the average measurement result is obtained. In other words, herein, not the measurement result of the individual sample 109, but the average measurement result for the group of the plurality of samples 109 is obtained. The measurement mode may be a mode of continuously measuring the adjacent samples 109 or a mode of discretely measuring the samples at a certain number interval.

Figure 7:
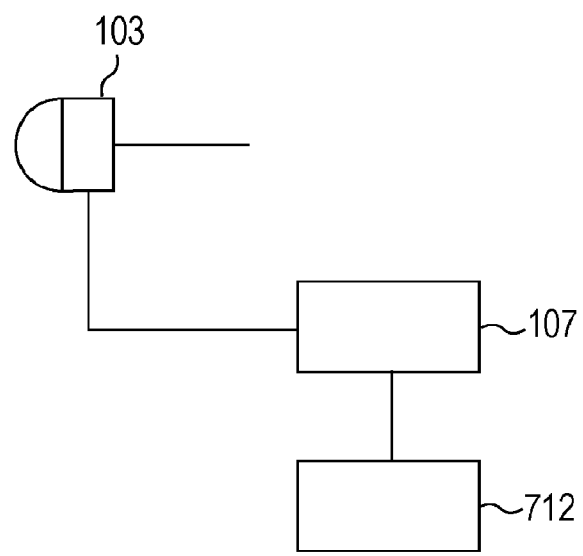
FIG. 7 is a schematic configuration diagram of a part of the apparatus according to the sixth embodiment of the present invention.

It is noted that in FIG. 6, the processing unit 107 carries out the accumulation processing on the basis of the number of the samples 109 to be measured, but the present invention is not limited to this mode. For example, as illustrated in FIG. 7, such a configuration may also be adopted that a counter unit 712 configured to divide the measurement time accumulates the data measured by the detection unit 103 in the predetermined measurement time.

Figure 8:
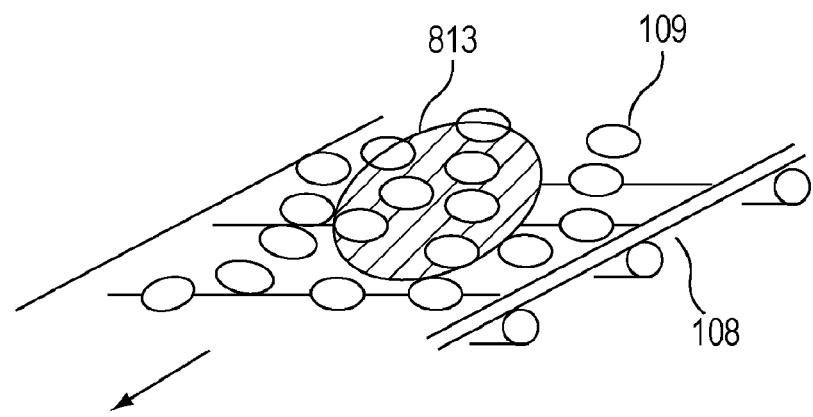
FIG. 8 is an explanatory diagram for describing an irradiation mode example of terahertz waves.

Also, according to the above-described embodiments, such a mode has been described that the terahertz waves are sequentially irradiated to the individual sample 109, but the present invention is not limited to this mode. For example, as illustrated in FIG. 8, such a configuration may also be adopted that by widening the irradiation area of the terahertz waves, the plurality of samples 109 are collectively irradiated with the terahertz waves.

In this manner, by providing the configuration of accumulating the responses from the plurality of objects to be measured, it is possible to mitigate the influence of the noise depending on the measurement system or the measurement environment, and the improvement in the signal detection accuracy is expected.

Seventh Embodiment

Fiber Laser

The present embodiment illustrates a mode related to the terahertz wave detection apparatus. To be specific, the present embodiment relates to a modification example of the laser unit 101. It is noted that a part of the description common to the above-described embodiment will be omitted.

According to the above-described embodiments, a titanium-sapphire laser is used for the laser unit 101, but according to the present embodiment, a fiber laser is used.

Figure 11:
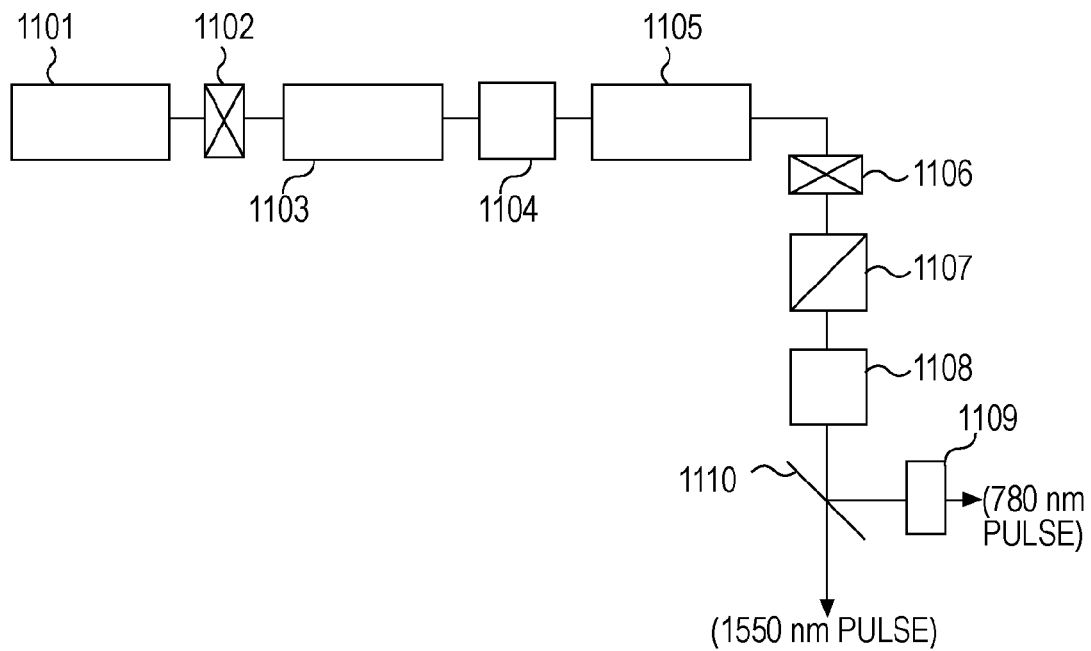
FIG. 11 is an explanatory diagram for describing a structure of a fiber laser.

The fiber laser is a small and stable ultrashort pulse laser source which is, mainly, an optical laser. A configuration example of the fiber laser is illustrated in FIG. 11. As illustrated in FIG. 11, the fiber laser is realized by including the following components:

A femtosecond fiber laser 1101
½ wavelength plates 1102 and 1106
An amplification unit 1103
An isolator 1104
A dispersion compensation unit 1105
A polarizing beam splitter 1107
A PPLN (Periodically Poled Lithium Niobate) element 1108 which is an efficient wavelength conversion element
A green cut filter 1109
A dichroic mirror 1110

The femtosecond fiber laser 1101 uses the optical laser for an oscillation medium. The center wavelength is 1558 nm, the average intensity is 5 mW, the pulse width is 300 fsec, and the cyclic frequency is 48 MHz. The femtosecond fiber laser 1101 of this type is smaller and more stable as compared with a solid-state laser. The ½ wavelength plates 1102 and 1106 are used for adjusting the polarization. The amplification unit 1103 is a part configured to amplify the intensity of the light pulse from the femtosecond fiber laser 1101. The light pulse whose intensity is amplified by the amplification unit 1103 is converted into a short pulse by the dispersion compensation unit 1105. The PPLN 1108 is a part configured to generate a component of 780 nm which is the second order harmonic component of the light pulse converted into the short pulse. After that, by using the green cut filter 1109 and the dichroic mirror 1110, the harmonic component 780 nm as well as the reference wave component 1550 nm are output at a desired branching ratio. This harmonic component is equivalent to the absorbing wavelength of LT-GaAs, and is used for the exciting light of the photoconductive element according to the present embodiment. It is noted that in a case where InGaAs is used for the semiconductor thin film used for the photoconductive element, the reference wave component can also be used for the exciting light for exciting the carrier. In this case, the optical system for generating and taking out the higher harmonic wave can also be omitted.

Hereinafter, details related to the amplification unit 1103 and the dispersion compensation unit 1105 will be described.

Figure 12:
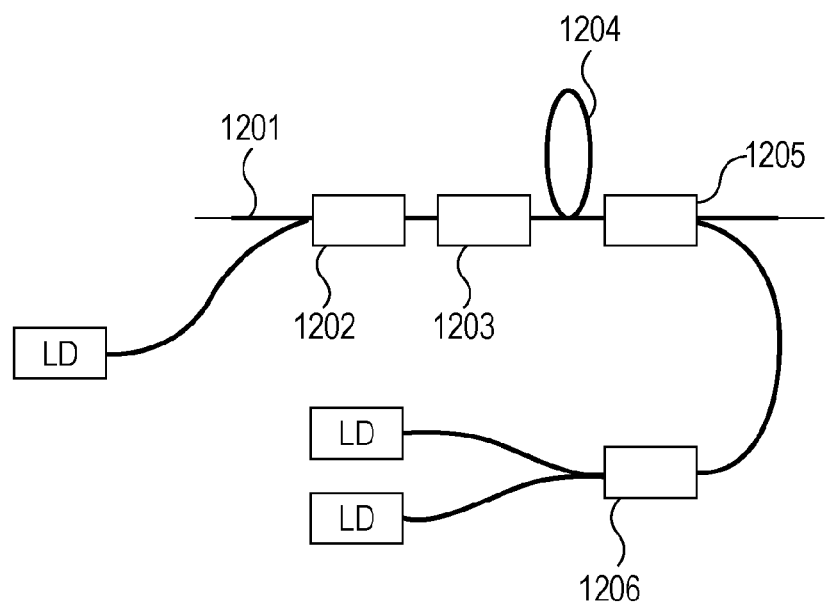
FIG. 12 is an explanatory diagram for describing an amplification unit of the fiber laser of FIG. 11.

FIG. 12 illustrates a configuration example of the amplification unit 1103. As illustrated in FIG. 12, the amplification unit 1103 is realized by including the following components:

Three laser diodes (which are referred to as LDs in the drawing)

A single mode fiber 1201

WDM (Wavelength Division Multiplexing) couplers 1202 and 1205

A polarization controller 1203

An Er (erbium) added fiber 1204

A polarization beam combiner 1206

With respect to the wavelength of 1.56 μm, the single mode fiber 1201 has the second order group velocity dispersion of −21.4 ps²/km, the mode field radius of 9.3 μm, the nonlinear coefficient of 1.89 W⁻¹ km⁻¹, and the fiber length of 4.5 m. With respect to the wavelength of 1.56 μm, the Er added fiber 1204 has the second order group velocity dispersion of 6.44 ps²/km, the mode field radius of 8.0 μm, the nonlinear coefficient of 2.55 W⁻¹ km⁻¹, and the fiber length of 6.0 m. The three LDs has the wavelength of 1480 nm and the intensity of 400 mW. As illustrated in FIG. 12, one of the LDs is used for forward excitation, and two of the LDs are used for backward excitation.

The pulse width of the light pulse incoming from the femtosecond fiber laser 1101 is expanded in the single mode fiber 1201 due to an influence of group velocity dispersion. With this configuration, the peak intensity of the light pulse is temporarily suppressed. As a result, the light pulse can suppress the excess nonlinear effect generated at the time of the propagation in the Er added fiber 1204, and therefore it is possible to carry out the effective energy amplification. According to this configuration, the average intensity of the light pulses can be expected to be about 20 dB.

Figure 13:
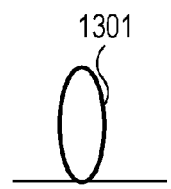
FIG. 13 is an explanatory diagram for describing a dispersion compensation unit of the fiber laser of FIG. 11.

FIG. 13 illustrates a configuration example of the dispersion compensation unit 1105. The dispersion compensation unit 1105 has a dispersion characteristic which is inverse to the dispersion characteristic generated by the amplification unit 1103. The light pulse output from the amplification unit 1103 has a tendency to have the band widely spread due to an influence of the self-phase modulation generated in the Er added fiber 1204. In view of the above, in the dispersion compensation unit 1105, the dispersion in the respective wavelengths is compensated, so that a pulse shorter than the pulse width of the femtosecond fiber laser 1101 is obtained. As illustrated in FIG. 13, according to the present embodiment, a dispersion compensation fiber 1301 is used for the dispersion compensation unit 1105. To be specific, as the dispersion compensation fiber 1301, a large hole diameter photonic crystal fiber is used. With respect to the wavelength of 1.56 μm, the dispersion compensation fiber 1301 used in the present embodiment has the second order group velocity dispersion of −30.3 ps²/km, the mode field radius of 26 μm, the nonlinear coefficient of 0.182 W⁻¹ km⁻¹, and the fiber length of 0.42 m. With this configuration, the obtained pulse width of the light pulse can be expected to be about 55 fsec, and the average intensity can be expected to be about 280 mW.

As described above, for the semiconductor thin film of the photoconductive element, in a case where LT-GaAs is used, the second higher harmonic wave is generated by the PPLN 1108 to obtain the exciting light. In the PPLN 1108, in addition to this harmonic component (780 nm), the reference wave component (1550 nm) is output, and thus, the dichroic mirror 1110 is used for separation. Also, in the PPLN 1108, in addition to the second higher harmonic wave, green light which is the third higher harmonic wave is slightly generated, and thus the green light is removed by the green cut filter 1109. According to such a configuration, the pulse width of the light pulse in the 780 nm band can be expected to be about 58 fsec, and the average intensity can be expected to be about 60 mW. Also, the pulse width of the light pulse in the 1550 nm band can be expected to be about 64 fsec, and the average intensity can be expected to be about 170 mW.

Figure 14A:
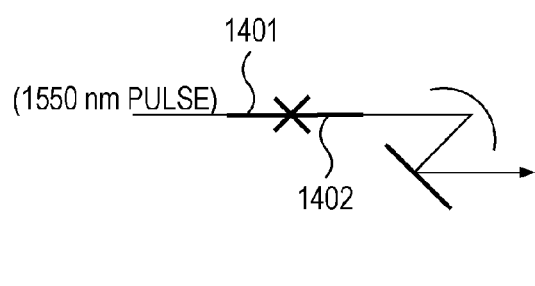
FIGS. 14A and 14B are explanatory diagrams for describing a structure for carrying out pulse compression.
Figure 14B:
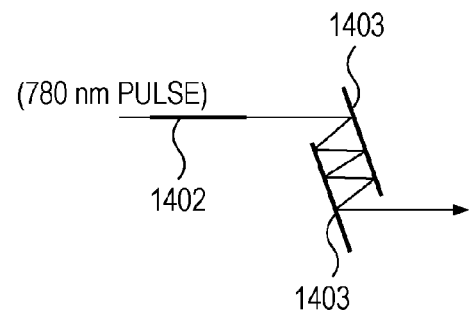

In some cases, as illustrated in FIGS. 14A and 14B, it is also possible to carry out the pulse compression by using the highly-nonlinear fiber. FIG. 14A is a structural drawing for compressing the light pulse in the 1550 nm band. Also, FIG. 14B is a structural drawing for compressing the light pulse in the 780 nm band. It is noted that these configurations are merely an example mode, and the method of carrying out the pulse compression is not limited to this method.

In FIG. 14A, in order to carry out the pulse compression in the 1550 nm band, a single mode fiber 1401 and a highly-nonlinear fiber 1402 are used. With respect to the wavelength 1.56 μm, the single mode fiber 1401 has the second order group velocity dispersion of −21.4 ps²/km, the nonlinear coefficient of 1.89 W⁻¹ km⁻¹, and the fiber length of 0.115 m. With respect to the wavelength 1.56 μm, the highly-nonlinear fiber 1402 has the second order group velocity dispersion of −14.6 ps²/km, the nonlinear coefficient of 4.53 W⁻¹ km⁻¹, and the fiber length of 0.04 m. Also, the light pulse output from the fiber has a parabolic mirror to collimate so as to avoid the pulse spread due to the dispersion in the lens. According to such a configuration, the obtained pulse width of the light pulse can be expected to be about 22 fsec, and the average intensity can be expected to be about 120 mW.

In FIG. 14B, in order to carry out the pulse compression in the 780 nm band, the highly-nonlinear fiber 1402 and a chirped mirror 1403 are used. The chirped mirror 1403 is a negative dispersion chirped mirror. Each time the mirror has one reflection, a dispersion of about −35 fs² is applied. While the light pulse is reflected between the chirped mirrors 1403 by plural times, the pulse compression is carried out. Herein, 1 m of the highly-nonlinear fiber 1402 is used. According to such a configuration, the obtained pulse width of the light pulse can be expected to be about 37 fsec, and the average intensity can be expected to be about 30 mW. According to the present embodiment, this light pulse is used as the exciting light of the photoconductive element. It is noted that the specific configuration and the respective parameters of the fiber laser are not limited to the above, and can be appropriately selected in accordance with various purposes by one of ordinary skill.

Also, according to the present embodiment, the photoconductive element is used for the generation unit 102. As described above, by using the semiconductor substrate having no electrodes or the organic crystal, it is possible to suppress the limitation of the terahertz wave band due to the electrode configuration, and the response waveform of a still wider band (the narrow pulse width) can be expected. To be specific, DAST crystal (4-dimethylamino-N-methyl-4-stilbazolium tosylate) is used for the generation unit 102, and the photoconductive element based on LT-gaas is used for the detection unit 103. At this time, from the fiber laser, by irradiating the light in the 1550 nm band as the probe light and the light in the 780 nm as the probe light, it is possible to generate the terahertz wave having the half bandwidth of about 200 fs (the band to about 7.5 THz).

In this manner, by using the fiber laser for the laser unit 101, stability, a smaller size, and a lower price for the apparatus can be expected.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2007-226338 filed Aug. 31, 2007 and No. 2008-159315 filed Jun. 18, 2008, which are hereby incorporated by reference herein in their entirety.

What is claimed is:

1. An apparatus for obtaining information related to terahertz waves transmitted through or reflected by a sample, the apparatus comprising:
   a generation unit arranged to generate terahertz waves;
   a detection unit arranged to detect terahertz waves which are generated by the generation unit and transmitted through or reflected by a sample;
   a delay unit arranged to change a timing for the detection unit to detect the terahertz waves;
   a storage unit arranged to pre-store information related to internal information of the sample as a standard information;
   a waveform obtaining unit arranged to obtain a temporal waveform of the transmitted or reflected terahertz waves which are obtained by the delay unit; and
   a delay time adjustment unit arranged to control the delay unit on the basis of the standard information pre-stored in the storage unit,
   wherein the terahertz waves from the sample include a first pulse and a second pulse,
   wherein the delay time adjustment unit adjusts the delay unit in a discontinuous manner on the basis of a position on a time axis for the first pulse and the second pulse, and
   wherein the waveform obtaining unit reconstructs the temporal waveforms by providing a time interval between the first pulse and the second pulse.

2. The apparatus according to claim 1, wherein the information related to the sample pre-stored in the storage unit is a temporal waveform of the terahertz waves transmitted through or reflected by the sample, which is previously obtained by the waveform obtaining unit.

3. The apparatus according to claim 1, wherein the area is a pulse of the temporal waveform.

4. The apparatus according to claim 1, wherein the waveform obtaining unit obtains a temporal waveform of the terahertz waves transmitted through or reflected by the sample by sampling the terahertz waves detected by the detection unit on the basis of the timing changed by the delay unit.

5. The apparatus according to claim 1, wherein the delay unit changes at least one of the timing for generating the terahertz waves and the timing for detecting the terahertz waves.

6. The apparatus according to claim 1, wherein the information related to the sample is obtained on the basis of the temporal waveform of the transmitted or reflected terahertz waves in the area.

7. The apparatus according to claim 1, wherein the temporal waveform of the transmitted or reflected terahertz waves in the area is compared with the information pre-stored in the storage unit to derive a state of the sample.

8. The apparatus according to claim 1, further comprising a fiber laser configured to generate pulse laser light, wherein the fiber laser comprises:
   an optical fiber used as an oscillation medium of the pulse laser light;
   an amplification unit arranged to amplify an intensity of an optical pulse oscillated from the optical fiber; and
   a dispersion compensation unit arranged to reduce a width of the amplified optical pulse,
   wherein the generation unit comprises a photoconductive element configured to generate the terahertz waves through irradiation of the pulse laser light, and
   wherein the detection unit comprises a photoconductive element configured to detect the terahertz waves through the irradiation of the pulse laser light.

9. The apparatus according to claim 1,
   wherein the apparatus comprises a plurality of the detection units, the plurality of the detection units being arranged corresponding to propagating directions of the terahertz waves transmitted through or reflected by the sample; and
   wherein the apparatus further comprises a light path switching unit for propagating the terahertz waves to one of the plurality of detection units arranged corresponding to the propagation directions.

10. The apparatus according to claim 1,
    wherein the apparatus comprises a plurality of the detection units, the plurality of the detection units being arranged corresponding to propagating directions of the terahertz waves transmitted through or reflected by the sample; and
    wherein the apparatus further comprises a light path switching unit for propagating the terahertz waves to one of the plurality of detection units arranged corresponding to the propagation directions.

11. A method for obtaining information related to terahertz waves transmitted through or reflected by a sample, the method comprising the steps of:
    generating terahertz waves;
    detecting a first pulse of the terahertz waves that is transmitted through or reflected by a sample;
    obtaining a movement amount of a delay unit by using information related to the sample;
    moving the delay unit by the obtained movement amount;
    detecting a second pulse of the terahertz waves that is transmitted through or reflected by the sample;
    obtaining a state of the sample from the first pulse and the second pulse; and
    outputting or storing the state of the sample as an inspection result,
    wherein the sample comprises a plurality of reflection interfaces,
    wherein the information related to the sample is a distance between the reflection interfaces,
    wherein the moving amount of the delay unit is obtained by using the distance,
    wherein a state of the reflection interface is obtained from the first pulse and the second pulse,
    wherein a permissible error range of the distance is set, and
    wherein the sample indicating a characteristic feature out of the permissible error range is determined as a defective product.

* * * * *